(12) United States Patent
Messerly

(10) Patent No.: US 11,883,609 B2
(45) Date of Patent: Jan. 30, 2024

(54) AUTOMATIC DIMENSIONAL FRAME REFERENCE FOR FIBER OPTIC

(71) Applicant: Bard Access Systems, Inc., Salt Lake City, UT (US)

(72) Inventor: Shayne Messerly, Kaysville, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 93 days.

(21) Appl. No.: 17/357,186

(22) Filed: Jun. 24, 2021

(65) Prior Publication Data

US 2021/0402144 A1 Dec. 30, 2021

Related U.S. Application Data

(60) Provisional application No. 63/045,667, filed on Jun. 29, 2020.

(51) Int. Cl.
*A61B 34/20* (2016.01)
*A61M 25/01* (2006.01)
(Continued)

(52) U.S. Cl.
CPC .............. *A61M 25/01* (2013.01); *A61B 1/07* (2013.01); *A61B 5/06* (2013.01); *A61B 2034/2055* (2016.02)

(58) Field of Classification Search
CPC . A61M 25/01; A61B 1/07; A61B 5/06; A61B 2034/2055
See application file for complete search history.

(56) References Cited

U.S. PATENT DOCUMENTS

| 4,813,429 A | 3/1989 | Eshel et al. |
| 5,099,845 A | 3/1992 | Besz et al. |

(Continued)

FOREIGN PATENT DOCUMENTS

| DE | 102016109601 A1 | 11/2017 |
| EP | 2240111 A2 | 10/2010 |

(Continued)

OTHER PUBLICATIONS

PCT/US2018/026493 filed Apr. 6, 2018 International Search Report and Written Opinion dated Jun. 22, 2018.
(Continued)

*Primary Examiner* — Rochelle D Turchen
(74) *Attorney, Agent, or Firm* — Rutan & Tucker LLP

(57) ABSTRACT

Disclosed herein is a system, apparatus and method directed to placing a medical device into a body of a patient, each performing or including operations of providing a broadband incident light signal to a plurality of core fibers of a multi-core optical fiber, receiving reflected light signals of different spectral width, processing the reflected light signals associated with the plurality of core fibers to determine (i) a physical state of the multi-core optical fiber relating to the medical device including the multi-core optical fiber, and (ii) an orientation of the multi-core optical fiber relative to a reference frame of the body. Additional operations include generating a display illustrating the physical state of the multi-core optical fiber based at least on the orientation determined during processing of the reflected light. Typically, the display is a two-dimensional representation of the multi-core optical fiber in accordance with the determined orientation.

9 Claims, 15 Drawing Sheets

(51) Int. Cl.
*A61B 1/07* (2006.01)
*A61B 5/06* (2006.01)

(56) References Cited

U.S. PATENT DOCUMENTS

| | | | |
|---|---|---|---|
| 5,163,935 A | 11/1992 | Black et al. |
| 5,207,672 A | 5/1993 | Roth et al. |
| 5,211,165 A | 5/1993 | Dumoulin et al. |
| 5,275,151 A | 1/1994 | Shockey et al. |
| 5,423,321 A | 6/1995 | Fontenot |
| 5,454,807 A | 10/1995 | Lennox et al. |
| 5,517,997 A | 5/1996 | Fontenot |
| 5,622,170 A | 4/1997 | Schulz |
| 5,740,808 A | 4/1998 | Panescu et al. |
| 5,872,879 A | 2/1999 | Hamm |
| 5,873,842 A | 2/1999 | Brennen et al. |
| 5,879,306 A | 3/1999 | Fontenot et al. |
| 5,906,579 A | 5/1999 | Vander Salm et al. |
| 6,069,698 A | 5/2000 | Ozawa et al. |
| 6,081,741 A | 6/2000 | Hollis |
| 6,178,346 B1 | 1/2001 | Amundson et al. |
| 6,208,887 B1 | 3/2001 | Clarke |
| 6,319,227 B1 | 11/2001 | Mansouri-Ruiz |
| 6,343,227 B1 | 1/2002 | Crowley |
| 6,398,721 B1 | 6/2002 | Nakamura et al. |
| 6,485,482 B1 | 11/2002 | Belef |
| 6,564,089 B2 | 5/2003 | Izatt et al. |
| 6,593,884 B1 | 7/2003 | Gilboa et al. |
| 6,597,941 B2 | 7/2003 | Fontenot et al. |
| 6,650,923 B1 | 11/2003 | Lesh et al. |
| 6,685,666 B1 | 2/2004 | Fontenot |
| 6,687,010 B1 | 2/2004 | Horii et al. |
| 6,690,966 B1 | 2/2004 | Rava et al. |
| 6,701,181 B2 | 3/2004 | Tang et al. |
| 6,711,426 B2 | 3/2004 | Benaron et al. |
| 6,816,743 B2 | 11/2004 | Moreno et al. |
| 6,892,090 B2 | 5/2005 | Verard et al. |
| 6,895,267 B2 | 5/2005 | Panescu et al. |
| 7,132,645 B2 | 11/2006 | Korn |
| 7,273,056 B2 | 9/2007 | Wilson et al. |
| 7,344,533 B2 | 3/2008 | Pearson et al. |
| 7,366,562 B2 | 4/2008 | Dukesherer et al. |
| 7,366,563 B2 | 4/2008 | Kleen et al. |
| 7,396,354 B2 | 7/2008 | Rychnovsky et al. |
| 7,406,346 B2 | 7/2008 | Kleen et al. |
| 7,515,265 B2 | 4/2009 | Alfano et al. |
| 7,532,920 B1 | 5/2009 | Ainsworth et al. |
| 7,587,236 B2 | 9/2009 | Demos et al. |
| 7,603,166 B2 | 10/2009 | Casscells, III et al. |
| 7,729,735 B1 | 6/2010 | Burchman |
| 7,757,695 B2 | 7/2010 | Wilson et al. |
| 7,758,499 B2 | 7/2010 | Adler |
| 7,840,253 B2 | 11/2010 | Tremblay et al. |
| 7,992,573 B2 | 8/2011 | Wilson et al. |
| 8,032,200 B2 | 10/2011 | Tearney et al. |
| 8,054,469 B2 | 11/2011 | Nakabayashi et al. |
| 8,060,187 B2 | 11/2011 | Marshik-Geurts et al. |
| 8,073,517 B1 | 12/2011 | Burchman |
| 8,078,261 B2 | 12/2011 | Imam |
| 8,187,189 B2 | 5/2012 | Jung et al. |
| 8,267,932 B2 | 9/2012 | Baxter et al. |
| 8,369,932 B2 | 2/2013 | Cinbis et al. |
| 8,388,541 B2 | 3/2013 | Messerly et al. |
| 8,571,640 B2 | 10/2013 | Holman |
| 8,597,315 B2 | 12/2013 | Snow et al. |
| 8,700,358 B1 | 4/2014 | Parker, Jr. |
| 8,781,555 B2 | 7/2014 | Burnside et al. |
| 8,798,721 B2 | 8/2014 | Dib |
| 8,968,331 B1 | 3/2015 | Sochor |
| 8,979,871 B2 | 3/2015 | Tyc et al. |
| 9,060,687 B2 | 6/2015 | Yamanaka et al. |
| 9,360,630 B2 | 6/2016 | Jenner et al. |
| 9,504,392 B2 | 11/2016 | Caron et al. |
| 9,560,954 B2 | 2/2017 | Jacobs et al. |
| 9,622,706 B2 | 4/2017 | Dick et al. |
| 9,678,275 B1 | 6/2017 | Griffin |
| 10,231,753 B2 | 3/2019 | Burnside et al. |
| 10,327,830 B2 | 6/2019 | Grant et al. |
| 10,349,890 B2 | 7/2019 | Misener et al. |
| 10,492,876 B2 | 12/2019 | Anastassiou et al. |
| 10,568,586 B2 | 2/2020 | Begin et al. |
| 10,631,718 B2 | 4/2020 | Petroff et al. |
| 10,992,078 B2 | 4/2021 | Thompson et al. |
| 11,123,047 B2 | 9/2021 | Jaffer et al. |
| 2002/0198457 A1 | 12/2002 | Tearney et al. |
| 2003/0092995 A1 | 5/2003 | Thompson |
| 2004/0242995 A1 | 12/2004 | Maschke |
| 2005/0033264 A1 | 2/2005 | Redinger |
| 2005/0261598 A1 | 11/2005 | Banet et al. |
| 2006/0013523 A1 | 1/2006 | Childers et al. |
| 2006/0036164 A1 | 2/2006 | Wilson et al. |
| 2006/0189959 A1 | 8/2006 | Schneiter |
| 2006/0200049 A1 | 9/2006 | Leo et al. |
| 2006/0241395 A1 | 10/2006 | Kruger et al. |
| 2006/0241492 A1 | 10/2006 | Boese et al. |
| 2007/0156019 A1 | 7/2007 | Larkin et al. |
| 2007/0201793 A1 | 8/2007 | Askins et al. |
| 2007/0287886 A1 | 12/2007 | Saadat |
| 2007/0299425 A1 | 12/2007 | Waner et al. |
| 2008/0039715 A1 | 2/2008 | Wilson et al. |
| 2008/0082004 A1 | 4/2008 | Banet et al. |
| 2008/0172119 A1 | 7/2008 | Yamasaki et al. |
| 2008/0183128 A1 | 7/2008 | Morriss et al. |
| 2008/0285909 A1 | 11/2008 | Younge et al. |
| 2009/0062634 A1 | 3/2009 | Say et al. |
| 2009/0137952 A1 | 5/2009 | Ramamurthy et al. |
| 2009/0234328 A1 | 9/2009 | Cox et al. |
| 2009/0304582 A1 | 12/2009 | Rousso et al. |
| 2009/0314925 A1 | 12/2009 | Van Vorhis et al. |
| 2010/0016729 A1 | 1/2010 | Futrell |
| 2010/0030063 A1 | 2/2010 | Lee et al. |
| 2010/0114115 A1 | 5/2010 | Schlesinger et al. |
| 2010/0286531 A1 | 11/2010 | Ryan et al. |
| 2010/0312095 A1 | 12/2010 | Jenkins et al. |
| 2011/0144481 A1 | 6/2011 | Feer et al. |
| 2011/0166442 A1 | 7/2011 | Sarvazyan |
| 2011/0172680 A1 | 7/2011 | Younge et al. |
| 2011/0237958 A1 | 9/2011 | Onimura |
| 2011/0245662 A1 | 10/2011 | Eggers et al. |
| 2011/0295108 A1 | 12/2011 | Cox et al. |
| 2011/0313280 A1 | 12/2011 | Govari et al. |
| 2012/0046562 A1 | 2/2012 | Powers et al. |
| 2012/0101413 A1 | 4/2012 | Beetel et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0321243 A1 | 12/2012 | Younge et al. |
| 2013/0028554 A1 | 1/2013 | Wong et al. |
| 2013/0096482 A1 | 4/2013 | Bertrand et al. |
| 2013/0104884 A1 | 5/2013 | Vazales et al. |
| 2013/0188855 A1 | 7/2013 | Desjardins et al. |
| 2013/0204124 A1 | 8/2013 | Duindam et al. |
| 2013/0211246 A1 | 8/2013 | Parasher |
| 2013/0296693 A1 | 11/2013 | Wenzel et al. |
| 2013/0310668 A1 | 11/2013 | Young |
| 2013/0324840 A1 | 12/2013 | Zhongping et al. |
| 2014/0121468 A1 | 5/2014 | Eichenholz |
| 2014/0221829 A1 | 8/2014 | Maitland et al. |
| 2014/0275997 A1 | 9/2014 | Chopra et al. |
| 2015/0029511 A1* | 1/2015 | 'T Hooft ............... G01L 1/246 |
| | | 356/477 |
| 2015/0031987 A1 | 1/2015 | Pameijer et al. |
| 2015/0080688 A1 | 3/2015 | Cinbis et al. |
| 2015/0099979 A1 | 4/2015 | Caves et al. |
| 2015/0119700 A1 | 4/2015 | Liang et al. |
| 2015/0190221 A1 | 7/2015 | Schaefer et al. |
| 2015/0209113 A1 | 7/2015 | Burkholz et al. |
| 2015/0209117 A1 | 7/2015 | Flexman et al. |
| 2015/0254526 A1 | 9/2015 | Denissen |
| 2015/0320977 A1 | 11/2015 | Vitullo et al. |
| 2016/0018602 A1 | 1/2016 | Govari et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |

(56) References Cited

U.S. PATENT DOCUMENTS

| | | |
|---|---|---|
| 2016/0213432 A1 | 7/2016 | Flexman et al. |
| 2016/0354038 A1 | 12/2016 | Demirtas et al. |
| 2017/0020394 A1 | 1/2017 | Harrington |
| 2017/0079681 A1 | 3/2017 | Burnside et al. |
| 2017/0082806 A1 | 3/2017 | Van Der Mark et al. |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0311901 A1 | 11/2017 | Zhao et al. |
| 2017/0319279 A1 | 11/2017 | Fish et al. |
| 2018/0095231 A1 | 4/2018 | Lowell et al. |
| 2018/0113038 A1 | 4/2018 | Janabi-Sharifi et al. |
| 2018/0140170 A1 | 5/2018 | Van Putten et al. |
| 2018/0235709 A1 | 8/2018 | Donhowe et al. |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0279909 A1 | 10/2018 | Noonan et al. |
| 2018/0289390 A1 | 10/2018 | Amorizzo et al. |
| 2018/0289927 A1* | 10/2018 | Messerly ................ G01L 1/242 |
| 2018/0339134 A1 | 11/2018 | Leo |
| 2018/0360545 A1 | 12/2018 | Cole et al. |
| 2019/0059743 A1 | 2/2019 | Ramachandran et al. |
| 2019/0110844 A1 | 4/2019 | Misener et al. |
| 2019/0231272 A1 | 8/2019 | Yamaji |
| 2019/0237902 A1 | 8/2019 | Thompson et al. |
| 2019/0307331 A1 | 10/2019 | Saadat et al. |
| 2019/0321110 A1 | 10/2019 | Grunwald et al. |
| 2019/0343424 A1 | 11/2019 | Blumenkranz et al. |
| 2019/0357875 A1 | 11/2019 | Qi et al. |
| 2019/0374130 A1 | 12/2019 | Bydlon et al. |
| 2020/0046434 A1 | 2/2020 | Graetzel et al. |
| 2020/0054399 A1 | 2/2020 | Duindam et al. |
| 2020/0305983 A1 | 10/2020 | Yampolsky et al. |
| 2020/0315770 A1 | 10/2020 | Dupont et al. |
| 2021/0045814 A1 | 2/2021 | Thompson et al. |
| 2021/0068911 A1 | 3/2021 | Walker et al. |
| 2021/0298680 A1 | 3/2021 | Sowards et al. |
| 2021/0244311 A1 | 8/2021 | Zhao et al. |
| 2021/0268229 A1 | 9/2021 | Sowards et al. |
| 2021/0271035 A1 | 9/2021 | Sowards et al. |
| 2021/0275257 A1 | 9/2021 | Prior et al. |
| 2021/0401456 A1 | 12/2021 | Cox et al. |
| 2021/0401509 A1 | 12/2021 | Misener et al. |
| 2022/0011192 A1 | 1/2022 | Misener et al. |
| 2022/0034733 A1 | 2/2022 | Misener et al. |
| 2022/0096796 A1 | 3/2022 | McLaughlin et al. |
| 2022/0110695 A1 | 4/2022 | Sowards et al. |
| 2022/0152349 A1 | 5/2022 | Sowards et al. |
| 2022/0160209 A1 | 5/2022 | Sowards et al. |
| 2022/0172354 A1 | 6/2022 | Misener et al. |
| 2022/0211442 A1 | 7/2022 | McLaughlin et al. |
| 2022/0233246 A1 | 7/2022 | Misener et al. |
| 2022/0369934 A1 | 11/2022 | Sowards et al. |
| 2023/0081198 A1 | 3/2023 | Sowards et al. |
| 2023/0097431 A1 | 3/2023 | Sowards et al. |
| 2023/0101030 A1 | 3/2023 | Misener et al. |
| 2023/0108604 A1 | 4/2023 | Messerly et al. |
| 2023/0126813 A1 | 4/2023 | Sowards et al. |
| 2023/0243715 A1 | 8/2023 | Misener et al. |
| 2023/0248444 A1 | 8/2023 | Misener et al. |
| 2023/0251150 A1 | 8/2023 | Visener et al. |

FOREIGN PATENT DOCUMENTS

| | | | |
|---|---|---|---|
| EP | 3545849 A1 | 10/2019 | |
| EP | 3705020 A1 | 9/2020 | |
| KR | 20190098512 A | 8/2019 | |
| WO | 99/64099 A1 | 12/1999 | |
| WO | 1999064099 A1 | 12/1999 | |
| WO | 2006122001 A2 | 11/2006 | |
| WO | 2009/155325 A2 | 12/2009 | |
| WO | 2011121516 A2 | 10/2011 | |
| WO | 2011141830 A1 | 11/2011 | |
| WO | 2011150376 A1 | 12/2011 | |
| WO | 2012064769 A2 | 5/2012 | |
| WO | 2015074045 A2 | 5/2015 | |
| WO | 2016038492 A1 | 3/2016 | |
| WO | 2016/061431 A1 | 4/2016 | |
| WO | 2016051302 A1 | 4/2016 | |
| WO | 2018/096491 A1 | 5/2018 | |
| WO | 2019037071 A1 | 2/2019 | |
| WO | 2019/046769 A1 | 3/2019 | |
| WO | WO-2019070423 A1 * | 4/2019 | ......... G01D 5/35316 |
| WO | 2019230713 A1 | 12/2019 | |
| WO | 2020/182997 A1 | 9/2020 | |
| WO | 2021030092 A1 | 2/2021 | |
| WO | 2021108688 A1 | 6/2021 | |
| WO | 2021108697 A1 | 6/2021 | |
| WO | 2021/138096 A1 | 7/2021 | |
| WO | 2022/031613 A1 | 2/2022 | |
| WO | 2022/081723 A1 | 4/2022 | |
| WO | 2022150411 A1 | 7/2022 | |
| WO | 2022/164902 A1 | 8/2022 | |
| WO | 2022/245987 A1 | 11/2022 | |
| WO | 2023043954 A1 | 3/2023 | |
| WO | 2023049443 A1 | 3/2023 | |
| WO | 2023055810 A1 | 4/2023 | |
| WO | 2023076143 A1 | 5/2023 | |

OTHER PUBLICATIONS

U.S. Appl. No. 15/947,267, filed Apr. 6, 2018 Non-Final Office Action dated May 29, 2020.

U.S. Appl. No. 15/947,267, filed Apr. 6, 2018 Final Office Action dated Nov. 10, 2020.

PCT/US2020/044801 filed Aug. 3, 2020 International Search Report and Written Opinion dated Oct. 26, 2020.

U.S. Appl. No. 15/947,267, filed Apr. 6, 2018 Non-Final Office Action dated Mar. 12, 2021.

U.S. Appl. No. 15/947,267, filed Apr. 6, 2018 Final Office Action dated Jun. 30, 2021.

PCT/US2021/019713 filed Feb. 25, 2021 International Search Report and Written Opinion dated Jul. 6, 2021.

PCT/US2021/020079 filed Feb. 26, 2021 International Search Report and Written Opinion dated Jun. 4, 2021.

PCT/US2020/062396 filed Nov. 25, 2020 International Search Report and Written Opinion dated Mar. 2, 2021.

PCT/US2020/062407 filed Nov. 25, 2020 International Search Report and Written Opinion dated Mar. 11, 2021.

PCT/US2021/020732 filed Mar. 3, 2021 International Search Report and Written Opinion dated Jul. 5, 2021.

PCT/US2021/038954 filed Jun. 24, 2021 International Search Report and Written Opinion dated Oct. 28, 2021.

PCT/US2021/041128 filed Jul. 9, 2021 International Search Report and Written Opinion dated Oct. 25, 2021.

U.S. Appl. No. 15/947,267, filed Apr. 6, 2018 Non-Final Office Action dated Oct. 13, 2021.

PCT/US2022/011347 filed Jan. 5, 2022 International Search Report and Written Opinion dated May 3, 2022.

PCT/US2022/013897 filed Jan. 26, 2022 International Search Report and Written Opinion dated May 11, 2022.

U.S. Appl. No. 15/947,267, filed Apr. 6, 2018 Final Office Action dated Apr. 22, 2022.

PCT/US2021/038899 filed Jun. 24, 2021 International Search Report and Written Opinion dated Oct. 6, 2021.

PCT/US2021/044216 filed Aug. 2, 2021 International Search Report and Written Opinion dated Nov. 18, 2021.

PCT/US2021/054802 filed Oct. 13, 2021 International Search Report and Written Opinion dated Feb. 2, 2022.

U.S. Appl. No. 17/185,777, filed Feb. 25, 2021 Non-Final Office Action dated Feb. 9, 2022.

PCT/US2020/062396 filed Nov. 25, 2020 International Preliminary Report on Patentability dated Jan. 29, 2021.

(56) References Cited

OTHER PUBLICATIONS

PCT/US2020/062407 filed Nov. 25, 2020 International Preliminary Report on Patentability dated Jan. 25, 2021.
U.S. Appl. No. 17/105,259, filed Nov. 25, 2020, Notice of Allowance dated Jul. 20, 2022.
U.S. Appl. No. 17/357,561, filed Jun. 24, 2021 Non-Final Office Action dated Aug. 11, 2022.
U.S. Appl. No. 17/371,993, filed Jul. 9, 2021 Non-Final Office Action dated Jul. 12, 2022.
Jackle Sonja et al. "Three-dimensional guidance including shape sensing of a stentgraft system for endovascular aneurysm repair." International Journal of Computer Assisted Radiology and Surgery, Springer DE. vol. 15, No. 6, May 7, 2020.
PCT/US2022/029894 filed May 18, 2022, International Search Report and Written Opinion dated Sep. 1, 2022.
PCT/US2022/043706 filed Sep. 16, 2022 International Search Report and Written Opinion dated Nov. 24, 2022.
PCT/US2022/044696 filed Sep. 26, 2022 International Search Report and Written Opinion dated Jan. 23, 2023.
PCT/US2022/045051 filed Sep. 28, 2022 International Search Report and Written Opinion dated Jan. 2, 2023.
PCT/US2022/047538 filed Oct. 24, 2022 International Search Report and Written Opinion dated Jan. 26, 2023.
U.S. Appl. No. 15/947,267, filed Apr. 6, 2018 Examiner's Answer dated Nov. 28, 2022.
U.S. Appl. No. 17/357,561, filed Jun. 24, 2021 Notice of Allowance dated Dec. 9, 2022.
U.S. Appl. No. 17/371,993, filed Jul. 9, 2021 Notice of Allowance dated Nov. 3, 2022.
U.S. Appl. No. 17/392,002, filed Aug. 2, 2021, Non-Final Office Action dated Sep. 12, 2022.
U.S. Appl. No. 17/392,002, filed Aug. 2, 2021, Notice of Allowance dated Jan. 19, 2023.
Fiber Optic RealShape (FORS) technology—research. Philips. (Oct. 18, 2018). Retrieved Feb. 28, 2023, from https:// www.philips.com/a-w/research/research-programs/fors.html (Year: 2018).
U.S. Appl. No. 16/984,104, filed Aug. 3, 2020 Restriction Requirement dated Mar. 13, 2023.
U.S. Appl. No. 17/105,310, filed Nov. 25, 2020 Non-Final Office Action dated Feb. 22, 2023.
U.S. Appl. No. 17/392,002, filed Aug. 2, 2021, Corrected Notice of Allowability dated Feb. 23, 2023.
U.S. Appl. No. 17/500,678, filed Oct. 13, 2021 Non-Final Office Action dated Mar. 15, 2023.
EP 20853352.1 filed Mar. 7, 2022 Extended European Search Report dated Jul. 27, 2023.
PCT/US2023/019239 filed Apr. 20, 2023 International Search Report and Written Opinion dated Jul. 20, 2023.
PCT/US2023/026487 filed Jun. 28, 2023 International Search Report and Written Opinion dated Sep. 6, 2023.
U.S. Appl. No. 16/984,104, filed Aug. 3, 2020 Non-Final Office Action dated Jun. 22, 2023.
U.S. Appl. No. 17/105,310, filed Nov. 25, 2020 Notice of Allowance dated Aug. 2, 2023.
U.S. Appl. No. 16/984,104, filed Aug. 3, 2020 Final Office Action dated Sep. 21, 2023.
U.S. Appl. No. 17/500,678, filed Oct. 13, 2021 Final Office Action dated Sep. 21, 2023.

* cited by examiner

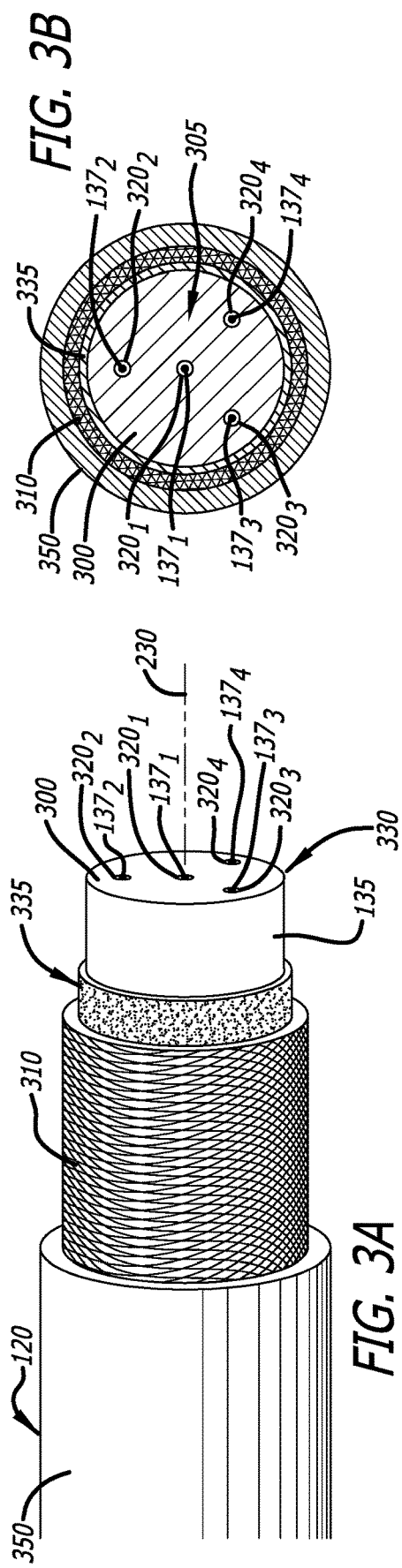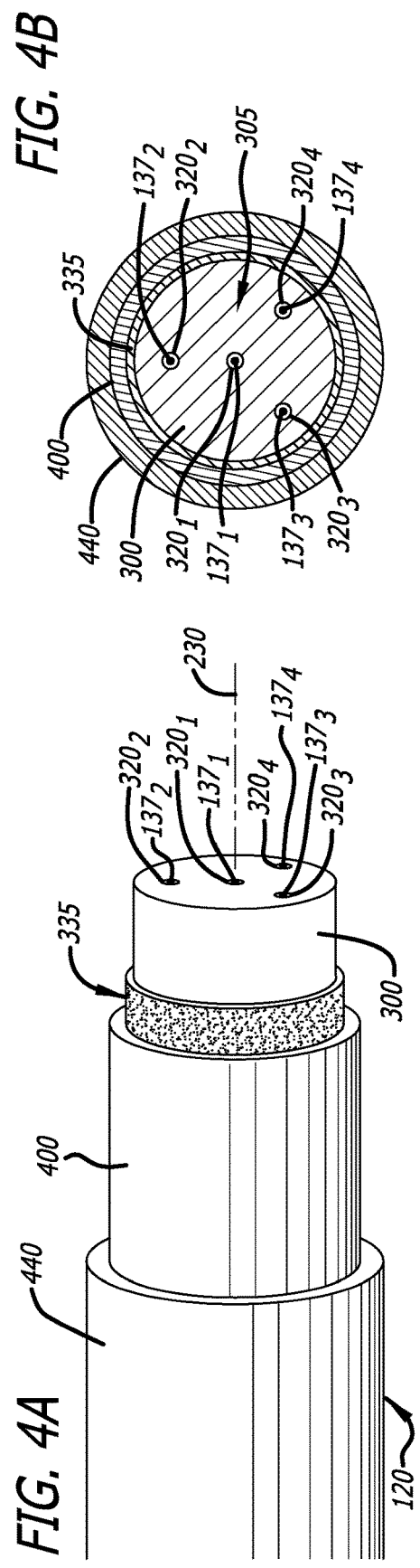

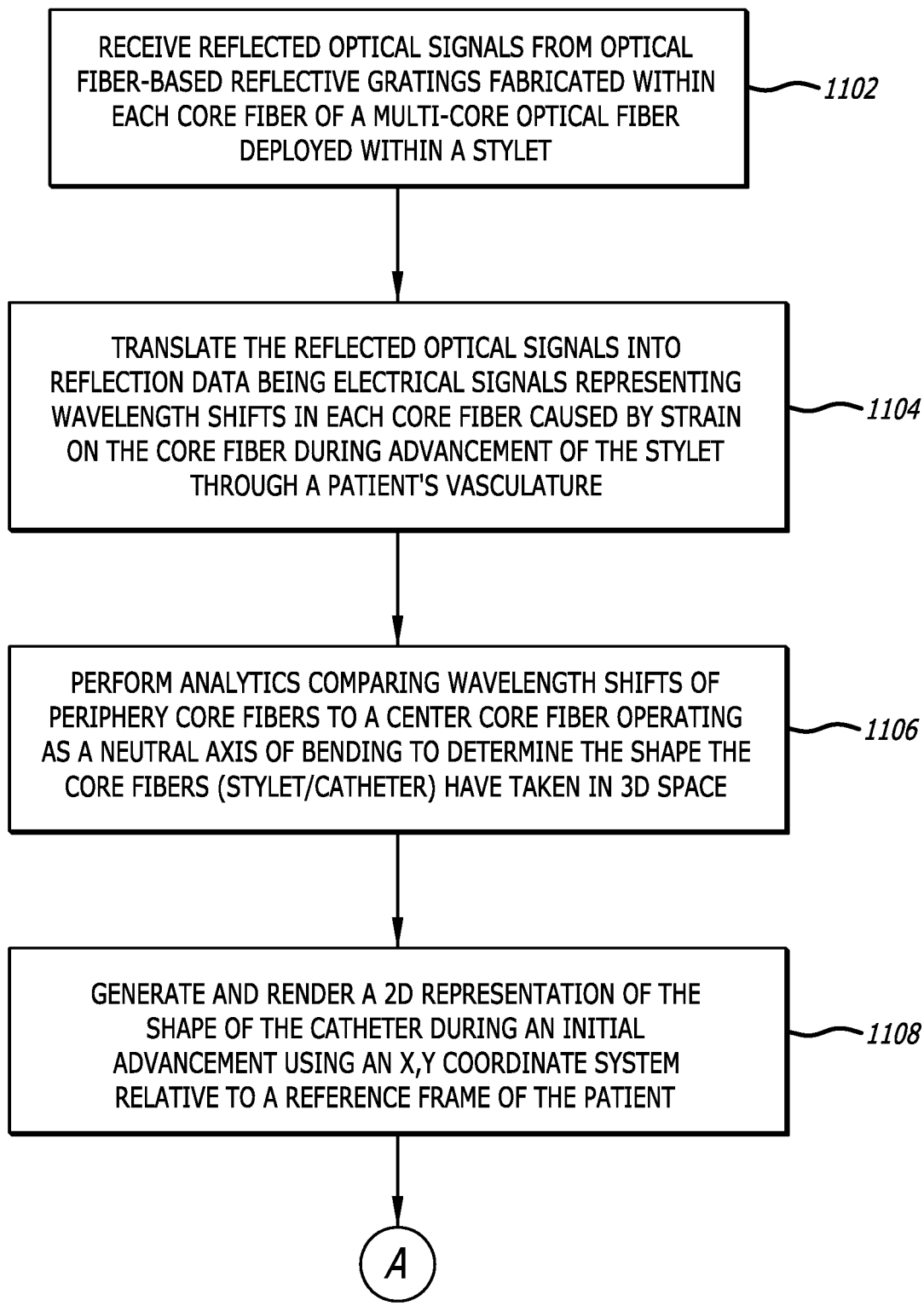

AUTOMATIC DIMENSIONAL FRAME REFERENCE FOR FIBER OPTIC

PRIORITY

This application claims the benefit of priority to U.S. Provisional Application No. 63/045,667, filed Jun. 29, 2020, which is incorporated by reference in its entirety into this application.

BACKGROUND

In the past, certain intravascular guidance of medical devices, such as guidewires and catheters for example, have used fluoroscopic methods for tracking tips of the medical devices and determining whether distal tips are appropriately localized in their target anatomical structures. However, such fluoroscopic methods expose patients and their attending clinicians to harmful X-ray radiation. Moreover, in some cases, the patients are exposed to potentially harmful contrast media needed for the fluoroscopic methods.

More recently, electromagnetic tracking systems have been used involving stylets. Generally, electromagnetic tracking systems feature three components: a field generator, a sensor unit and control unit. The field generator uses several coils to generate a position-varying magnetic field, which is used to establish a coordinate space. Attached to the stylet, such as near a distal end (tip) of the stylet for example, the sensor unit includes small coils in which current is induced via the magnetic field. Based on the electrical properties of each coil, the position and orientation of the medical device may be determined within the coordinate space. The control unit controls the field generator and captures data from the sensor unit.

Although electromagnetic tracking systems avoid line-of-sight reliance in tracking the tip of a stylet while obviating radiation exposure and potentially harmful contrast media associated with fluoroscopic methods, electromagnetic tracking systems are prone to interference. More specifically, since electromagnetic tracking systems depend on the measurement of magnetic fields produced by the field generator, these systems are subject to electromagnetic field interference, which may be caused by the presence of many different types of consumer electronics such as cellular telephones. Additionally, electromagnetic tracking systems are subject to signal drop out, depend on an external sensor, and are defined to a limited depth range.

Disclosed herein is a fiber optic shape sensing system and methods thereof, which is not subject to the disadvantages associated with electromagnetic tracking systems as described above and is capable in its current form of providing confirmation of tip placement or information passed/interpreted as an electrical signal. Further, inventive systems configured to and methods of determining an orientation of a stylet advancing within a patient's vasculature based at least partially on the information passed/interpreted as an electrical signal are disclosed. Additionally, such inventive systems and method that may perform or include operations of displaying information received from the fiber optic shape sensing system based on the determined orientation are disclosed.

SUMMARY

Briefly summarized, embodiments disclosed herein are directed to systems, apparatus and methods for obtaining three-dimensional (3D) information (reflected light) corresponding to a trajectory and/or shape of a medical instrument, such as a catheter, a guidewire, or a stylet, during advancement through a vasculature of a patient, determining an orientation of the medical instrument relative to the patient, and generating and rendering a two-dimensional (2D) display of the medical instrument in real-time in accordance with the determined orientation.

More particularly, in some embodiments, the medical instrument includes a multi-core optical fiber, with each core fiber of the multi-core optical fiber is configured with an array of sensors (reflective gratings), which are spatially distributed over a prescribed length of the core fiber to generally sense external strain those regions of the core fiber occupied by the sensor. The multi-core optical fiber is configured to receive broadband light from a console during advancement through the vasculature of a patient, where the broadband light propagates along at least a partial distance of the multi-core optical fiber toward the distal end. Given that each sensor positioned along the same core fiber is configured to reflect light of a different, specific spectral width, the array of sensors enables distributed measurements throughout the prescribed length of the multi-core optical fiber. These distributed measurements may include wavelength shifts having a correlation with strain experienced by the sensor.

The reflected light from the sensors (reflective gratings) within each core fiber of the multi-core optical fiber is returned from the medical instrument for processing by the console. The physical state of the medical instrument may be ascertained based on analytics of the wavelength shifts of the reflected light. For example, the strain caused through bending of the medical instrument, and hence angular modification of each core fiber, causes different degrees of deformation. The different degrees of deformation alters the shape of the sensors (reflective grating) positioned on the core fiber, which may cause variations (shifts) in the wavelength of the reflected light from the sensors positioned on each core fiber within the multi-core optical fiber, as shown in FIGS. 2, 7 and 10.

From this wavelength shifting, logic within the console may determine the physical state of the medical instrument (e.g., shape). Additionally, based on the wavelength shifting and anatomical constraints of the patient's body, the logic within the console may determine an orientation of the medical instrument relative to a known reference frame of the patient's body. Subsequently, the logic within the console is configured to generate a 2D display of the physical state of the medical instrument using the determined orientation of the medical instrument, where the reference frame of the 2D display mirrors the reference frame of the patient's body. Thus, the 2D display depicts a current physical state of the catheter displayed in such a manner as to be representative of the anatomical positioning and orientation relative to the patient's body, which enables a clinician to perceive the advancement of the medical instrument in an anatomically proper manner.

Specific embodiments of the disclosure include utilization of a stylet featuring a multi-core optical fiber and a conductive medium that collectively operate for tracking placement of a catheter or other medical device within a body of a patient. The stylet is configured to return information for use in identifying its physical state (e.g., shape length, shape, and/or form) of (i) a portion of the stylet (e.g., tip, segment of stylet, etc.) or a portion of a catheter inclusive of at least a portion of the stylet (e.g., tip, segment of catheter, etc.) or (ii) the entirety or a substantial portion of the stylet or catheter within the body of a patient (hereinafter, described as the "physical state of the stylet" or the "physical state of the catheter"). According to one embodiment of the disclosure, the returned information may be obtained from reflected light signals of different spectral widths, where each reflected light signal corresponds to a portion of broadband incident light propagating along a core of the multi-core optical fiber (hereinafter, "core fiber") that is reflected back over the core fiber by a particular sensor located on the core fiber. One illustrative example of the returned information may pertain to a change in signal characteristics of the reflected light signal returned from the sensor, where wavelength shift is correlated to (mechanical) strain on the core fiber.

In some embodiments, the stylet includes a multi-core optical fiber, where each core fiber utilizes a plurality of sensors and each sensor is configured to reflect a different spectral range of the incident light (e.g., different light frequency range). Based on the type and degree of strain asserted on each core fiber, the sensors associated with that core fiber may alter (shift) the wavelength of the reflected light to convey the type and degree of stain on that core fiber at those locations of the stylet occupied by the sensors. The sensors are spatially distributed at various locations of the core fiber between a proximal end and a distal end of the stylet so that shape sensing of the stylet may be conducted based on analytics of the wavelength shifts. Herein, the shape sensing functionality is paired with the ability to simultaneously pass an electrical signal through the same member (stylet) through conductive medium included as part of the stylet.

More specifically, in some embodiments each core fiber of the multi-core optical fiber is configured with an array of sensors, which are spatially distributed over a prescribed length of the core fiber to generally sense external strain those regions of the core fiber occupied by the sensor. Given that each sensor positioned along the same core fiber is configured to reflect light of a different, specific spectral width, the array of sensors enables distributed measurements throughout the prescribed length of the multi-core optical fiber. These distributed measurements may include wavelength shifts having a correlation with strain experienced by the sensor.

According to one embodiment of the disclosure, each sensor may operate as a reflective grating such as a fiber Bragg grating (FBG), namely an intrinsic sensor corresponding to a permanent, periodic refractive index change inscribed into the core fiber. Stated differently, the sensor operates as a light reflective mirror for a specific spectral width (e.g., a specific wavelength or specific range of wavelengths). As a result, as broadband incident light is supplied by an optical light source and propagates through a particular core fiber, upon reaching a first sensor of the distributed array of sensors for that core fiber, light of a prescribed spectral width associated with the first sensor is reflected back to an optical receiver within a console, including a display and the optical light source. The remaining spectrum of the incident light continues propagation through the core fiber toward a distal end of the stylet. The remaining spectrum of the incident light may encounter other sensors from the distributed array of sensors, where each of these sensors is fabricated to reflect light with different specific spectral widths to provide distributed measurements, as described above.

During operation, multiple light reflections (also referred to as "reflected light signals") are returned to the console from each of the plurality of core fibers of the multi-core optical fiber. Each reflected light signal may be uniquely associated with a different spectral width. Information associated with the reflected light signals may be used to determine a three-dimensional representation of the physical state of the stylet within the body of a patient. Herein, the core fibers are spatially separated with the cladding of the multi-mode optical fiber and each core fiber is configured to separately return light of different spectral widths (e.g., specific light wavelength or a range of light wavelengths) reflected from the distributed array of sensors fabricated in each of the core fibers. A comparison of detected shifts in wavelength of the reflected light returned by a center core fiber (operating as a reference) and the surrounding, periphery core fibers may be used to determine the physical state of the stylet.

During vasculature insertion and advancement of the catheter, the clinician may rely on the console to visualize a current physical state (e.g., shape) of a catheter guided by the stylet to avoid potential path deviations. As the periphery core fibers reside at spatially different locations within the cladding of the multi-mode optical fiber, changes in angular orientation (such as bending with respect to the center core fiber, etc.) of the stylet imposes different types (e.g., compression or tension) and degrees of strain on each of the periphery core fibers as well as the center core fiber. The different types and/or degree of strain may cause the sensors of the core fibers to apply different wavelength shifts, which can be measured to extrapolate the physical state of the stylet (catheter).

In order for the clinician to rely on the console to visualize the current physical state of the catheter, the console displays a visual representation, typically a 2D image, of the physical state of the catheter based on the reflected light. In generating the 2D image of the physical state of the catheter, the image must be displayed in such a manner as to be representative of the anatomical positioning relative to the patient's body. Thus, following analytics of the reflected light, logic of the console determines an orientation of the stylet relative to a known frame of reference of the patient's body. The logic then generates and renders a 2D display of the physical state of the catheter and a representation of the patient's body, with the display properly orienting the catheter relative to the patient's body based on the determined orientation of the stylet.

Although the reflected light provides a wealth of information capable of enabling extrapolation of the physical state of the stylet (catheter), such information lacks context as to the orientation of the stylet advancing within the patient's body. For instance, the wavelength shifts of the reflected light may indicate different degrees of deformation of each core fiber, which collectively may indicate a curvature of the stylet; however, the indication of such a curvature lacks context as to an orientation or direction with respect to the patient's body. Thus, the wavelength shifts of the reflected light, alone, do not enable the logic to generate a 2D display of the physical state of the catheter that is properly oriented within a visual representation of the patient's body.

Embodiments of the disclosure describe how the logic of the console utilizes the known anatomical constraints of the human body, a known insertion site of the stylet within the patient's body, and/or the wavelength shifts of the reflected light to determine an orientation of the stylet with respect to the patient's body. Additional embodiments further describe the generation of displays that illustrate the catheter within the patient's body based on the orientation of the stylet disposed within the catheter. Typically, such displays are 2D;

however, as the wavelength shifts of the reflected light provide 3D information, generation of 3D displays has also been considered.

Some embodiments of the invention disclose a method for placing a medical device into a body of a patient comprising providing a broadband incident light signal to each of a plurality of reflective gratings distributed along a length of each of a plurality of core fibers of a multi-core optical fiber, the plurality of core fibers being spatially distributed to experience different degrees of strain, receiving reflected light signals of different spectral widths of the broadband incident light by each of the plurality of reflective gratings, processing the reflected light signals received from each of the plurality of reflective gratings associated with the plurality of core fibers to determine (i) a physical state of the multi-core optical fiber relating to the medical device including the multi-core optical fiber, and (ii) an orientation of the multi-core optical fiber relative to a reference frame of the body.

Some of the embodiments further include generating a display illustrating the physical state of the multi-core optical fiber based at least on the orientation determined during processing of the reflected light. Additionally, the display may be a two-dimensional representation of the physical state of the multi-core optical fiber in accordance with the orientation determined during processing of the reflected light.

In some embodiments, the physical state of the multi-core optical fiber relating to the medical device includes one or more of a length, a shape or a form as currently possessed by the multi-core optical fiber. In further embodiments, the different types of strain include compression and tension.

In some instances, determining the orientation of the multi-core optical fiber relative to the reference frame of the body includes establishing the reference frame of the body utilizing a coordinate system, establishing an initial direction of advancement along a first axis of the coordinate system for the multi-core optical fiber based on the multi-core optical fiber entering the body at a known insertion site, correlating initial reflected light signals to the initial direction of advancement along the first axis of the coordinate system, detecting a curve in the advancement of the multi-core optical fiber based on processing of the reflected light signals, and correlating reflected light signals corresponding to the curve in the advancement with a second direction of advancement along a second axis of the coordinate system, wherein the orientation is defined by (i) the initial reflected light signals correlated with the initial direction of advancement along the first axis of the coordinate system, and (ii) the reflected light signals corresponding to the curve in the advancement correlated with the second direction of advancement along the second axis of the coordinate system. The medical device may include an elongated shape and is inserted into a vasculature of the body of the patient. In some embodiments, the medical device is a stylet removably inserted into a lumen of a catheter assembly for placement of a distal tip of the catheter assembly in a superior vena cava of the vasculature. Further, at least two of the plurality of core fibers may be configured to experience different types of strain in response to changes in an orientation of the multi-core optical fiber. In some embodiments, each reflective grating of the plurality of reflective gratings alters its reflected light signal by applying a wavelength shift dependent on a strain experienced by the reflective grating.

Some embodiments of the invention disclose non-transitory computer-readable medium having stored thereon logic that, when executed by the one or more processors, causes operations including providing a broadband incident light signal to each of a plurality of reflective gratings distributed along a length of each of a plurality of core fibers of a multi-core optical fiber, the plurality of core fibers being spatially distributed to experience different degrees of strain, receiving reflected light signals of different spectral widths of the broadband incident light by each of the plurality of reflective gratings, processing the reflected light signals received from each of the plurality of reflective gratings associated with the plurality of core fibers to determine (i) a physical state of the multi-core optical fiber relating to the medical device including the multi-core optical fiber, and (ii) an orientation of the multi-core optical fiber relative to a reference frame of the body.

Some of the embodiments further include generating a display illustrating the physical state of the multi-core optical fiber based at least on the orientation determined during processing of the reflected light. Additionally, the display may be a two-dimensional representation of the physical state of the multi-core optical fiber in accordance with the orientation determined during processing of the reflected light.

In some embodiments, the physical state of the multi-core optical fiber relating to the medical device includes one or more of a length, a shape or a form as currently possessed by the multi-core optical fiber. In further embodiments, the different types of strain include compression and tension.

In some instances, determining the orientation of the multi-core optical fiber relative to the reference frame of the body includes establishing the reference frame of the body utilizing a coordinate system, establishing an initial direction of advancement along a first axis of the coordinate system for the multi-core optical fiber based on the multi-core optical fiber entering the body at a known insertion site, correlating initial reflected light signals to the initial direction of advancement along the first axis of the coordinate system, detecting a curve in the advancement of the multi-core optical fiber based on processing of the reflected light signals, and correlating reflected light signals corresponding to the curve in the advancement with a second direction of advancement along a second axis of the coordinate system, wherein the orientation is defined by (i) the initial reflected light signals correlated with the initial direction of advancement along the first axis of the coordinate system, and (ii) the reflected light signals corresponding to the curve in the advancement correlated with the second direction of advancement along the second axis of the coordinate system. The medical device may include an elongated shape and is inserted into a vasculature of the body of the patient. In some embodiments, the medical device is a stylet removably inserted into a lumen of a catheter assembly for placement of a distal tip of the catheter assembly in a superior vena cava of the vasculature. Further, at least two of the plurality of core fibers may be configured to experience different types of strain in response to changes in an orientation of the multi-core optical fiber. In some embodiments, each reflective grating of the plurality of reflective gratings alters its reflected light signal by applying a wavelength shift dependent on a strain experienced by the reflective grating.

Some embodiments of the invention disclose a medical device comprising a multi-core optical fiber having a plurality of core fibers, each of the plurality of core fibers including a plurality of sensors distributed along a longitudinal length of a corresponding core fiber and each sensor of the plurality of sensors being configured to (i) reflect a light signal of a different spectral width based on received incident light, and (ii) change a characteristic of the reflected light signal for use in determining a physical state of the multi-core optical fiber, and a console including one or more processors and a non-transitory computer-readable medium having stored thereon logic that, when executed by the one or more processors, causing performance of certain operations. These certain operations may include providing a broadband incident light signal to each of a plurality of reflective gratings distributed along a length of each of a plurality of core fibers of a multi-core optical fiber, the plurality of core fibers being spatially distributed to experience different degrees of strain, receiving reflected light signals of different spectral widths of the broadband incident light by each of the plurality of reflective gratings, processing the reflected light signals received from each of the plurality of reflective gratings associated with the plurality of core fibers to determine (i) a physical state of the multi-core optical fiber relating to the medical device including the multi-core optical fiber, and (ii) an orientation of the multi-core optical fiber relative to a reference frame of the body.

Some of the embodiments further include generating a display illustrating the physical state of the multi-core optical fiber based at least on the orientation determined during processing of the reflected light. Additionally, the display may be a two-dimensional representation of the physical state of the multi-core optical fiber in accordance with the orientation determined during processing of the reflected light.

In some embodiments, the physical state of the multi-core optical fiber relating to the medical device includes one or more of a length, a shape or a form as currently possessed by the multi-core optical fiber. In further embodiments, the different types of strain include compression and tension.

In some instances, determining the orientation of the multi-core optical fiber relative to the reference frame of the body includes establishing the reference frame of the body utilizing a coordinate system, establishing an initial direction of advancement along a first axis of the coordinate system for the multi-core optical fiber based on the multi-core optical fiber entering the body at a known insertion site, correlating initial reflected light signals to the initial direction of advancement along the first axis of the coordinate system, detecting a curve in the advancement of the multi-core optical fiber based on processing of the reflected light signals, and correlating reflected light signals corresponding to the curve in the advancement with a second direction of advancement along a second axis of the coordinate system, wherein the orientation is defined by (i) the initial reflected light signals correlated with the initial direction of advancement along the first axis of the coordinate system, and (ii) the reflected light signals corresponding to the curve in the advancement correlated with the second direction of advancement along the second axis of the coordinate system. The medical device may include an elongated shape and is inserted into a vasculature of the body of the patient. In some embodiments, the medical device is a stylet removably inserted into a lumen of a catheter assembly for placement of a distal tip of the catheter assembly in a superior vena cava of the vasculature. Further, at least two of the plurality of core fibers may be configured to experience different types of strain in response to changes in an orientation of the multi-core optical fiber. In some embodiments, each reflective grating of the plurality of reflective gratings alters its reflected light signal by applying a wavelength shift dependent on a strain experienced by the reflective grating.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which:

FIG. 3A is a first exemplary embodiment of the stylet of FIG. 1A supporting both an optical and electrical signaling in accordance with some embodiments;

FIG. 3B is a cross sectional view of the stylet of FIG. 3A in accordance with some embodiments;

FIG. 4A is a second exemplary embodiment of the stylet of FIG. 1B in accordance with some embodiments;

FIG. 4B is a cross sectional view of the stylet of FIG. 4A in accordance with some embodiments;

FIGS. 11A-11B illustrate a flowchart of a second embodiment of operations performed by logic of the medical instrument monitoring system of FIG. 1A in accordance with some embodiments.

DETAILED DESCRIPTION

Figure 1A:
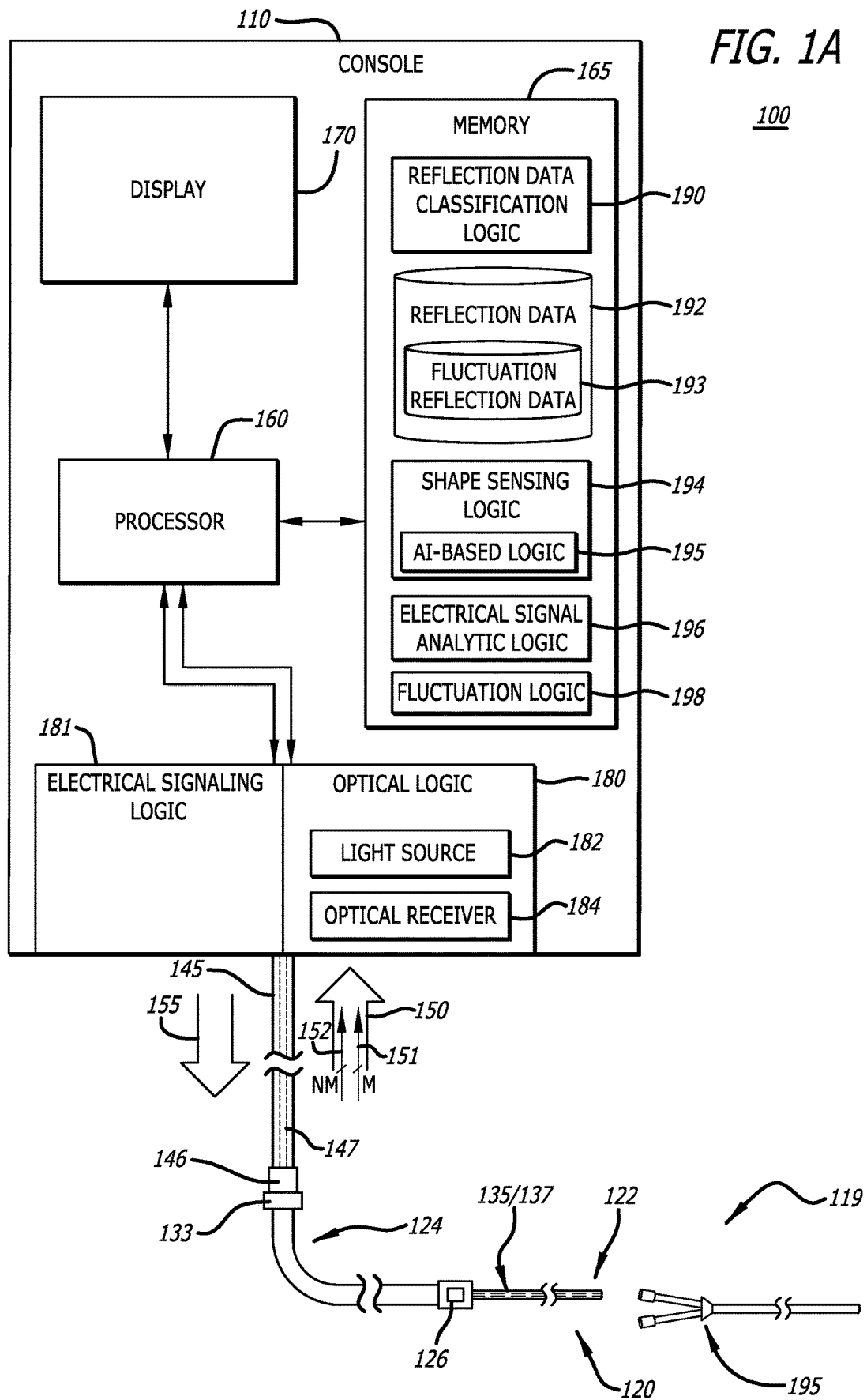
FIG. 1A is an illustrative embodiment of a medical instrument monitoring system including a medical instrument with optic shape sensing and fiber optic-based oximetry capabilities in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a probe disclosed herein includes a portion of the probe intended to be near a clinician when the probe is used on a patient. Likewise, a "proximal length" of, for example, the probe includes a length of the probe intended to be near the clinician when the probe is used on the patient. A "proximal end" of, for example, the probe includes an end of the probe intended to be near the clinician when the probe is used on the patient. The proximal portion, the proximal end portion, or the proximal length of the probe can include the proximal end of the probe; however, the proximal portion, the proximal end portion, or the proximal length of the probe need not include the proximal end of the probe. That is, unless context suggests otherwise, the proximal portion, the proximal end portion, or the proximal length of the probe is not a terminal portion or terminal length of the probe.

With respect to "distal," a "distal portion" or a "distal end portion" of, for example, a probe disclosed herein includes a portion of the probe intended to be near or in a patient when the probe is used on the patient. Likewise, a "distal length" of, for example, the probe includes a length of the probe intended to be near or in the patient when the probe is used on the patient. A "distal end" of, for example, the probe includes an end of the probe intended to be near or in the patient when the probe is used on the patient. The distal portion, the distal end portion, or the distal length of the probe can include the distal end of the probe; however, the distal portion, the distal end portion, or the distal length of the probe need not include the distal end of the probe. That is, unless context suggests otherwise, the distal portion, the distal end portion, or the distal length of the probe is not a terminal portion or terminal length of the probe.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit "ASIC", etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random access memory "RAM"); or persistent storage such as non-volatile memory (e.g., read-only memory "ROM", power-backed RAM, flash memory, phase-change memory, etc.), a solid-state drive, hard disk drive, an optical disc drive, or a portable memory device. As firmware, the logic may be stored in persistent storage.

Referring to FIG. 1A, an illustrative embodiment of a medical instrument monitoring system including a medical instrument with optic shape sensing and fiber optic-based oximetry capabilities is shown in accordance with some embodiments. As shown, the system 100 generally includes a console 110 and a stylet assembly 119 communicatively coupled to the console 110. For this embodiment, the stylet assembly 119 includes an elongate probe (e.g., stylet) 120 on its distal end 122 and a console connector 133 on its proximal end 124, where the stylet 120 is configured to advance within a patient vasculature either through, or in conjunction with, a catheter 195. The console connector 133 enables the stylet assembly 119 to be operably connected to the console 110 via an interconnect 145 including one or more optical fibers 147 (hereinafter, "optical fiber(s)") and a conductive medium terminated by a single optical/electric connector 146 (or terminated by dual connectors. Herein, the connector 146 is configured to engage (mate) with the console connector 133 to allow for the propagation of light between the console 110 and the stylet assembly 119 as well as the propagation of electrical signals from the stylet 120 to the console 110.

An exemplary implementation of the console 110 includes a processor 160, a memory 165, a display 170 and optical logic 180, although it is appreciated that the console 110 can take one of a variety of forms and may include additional components (e.g., power supplies, ports, interfaces, etc.) that are not directed to aspects of the disclosure. An illustrative example of the console 110 is illustrated in U.S. Publication No. 2019/0237902, the entire contents of which are incorporated by reference herein. The processor 160, with access to the memory 165 (e.g., non-volatile memory or non-transitory, computer-readable medium), is included to control functionality of the console 110 during operation. As shown, the display 170 may be a liquid crystal diode (LCD) display integrated into the console 110 and employed as a user interface to display information to the clinician, especially during a catheter placement procedure (e.g., cardiac catheterization). In another embodiment, the display 170 may be separate from the console 110. Although not shown, a user interface is configured to provide user control of the console 110.

For both of these embodiments, the content depicted by the display 170 may change according to which mode the stylet 120 is configured to operate: optical, TLS, ECG, or another modality. In TLS mode, the content rendered by the display 170 may constitute a two-dimensional (2D) or three-dimensional (3D) representation of the physical state (e.g., length, shape, form, and/or orientation) of the stylet 120 computed from characteristics of reflected light signals 150 returned to the console 110. The reflected light signals 150 constitute light of a specific spectral width of broadband incident light 155 reflected back to the console 110. According to one embodiment of the disclosure, the reflected light signals 150 may pertain to various discrete portions (e.g., specific spectral widths) of broadband incident light 155 transmitted from and sourced by the optical logic 180, as described below According to one embodiment of the disclosure, an activation control 126, included on the stylet assembly 119, may be used to set the stylet 120 into a desired operating mode and selectively alter operability of the display 170 by the clinician to assist in medical device placement. For example, based on the modality of the stylet 120, the display 170 of the console 110 can be employed for optical modality-based guidance during catheter advancement through the vasculature or TLS modality to determine the physical state (e.g., length, form, shape, orientation, etc.) of the stylet 120. In one embodiment, information from multiple modes, such as optical, TLS or ECG for example, may be displayed concurrently (e.g., at least partially overlapping in time).

Referring still to FIG. 1A, the optical logic 180 is configured to support operability of the stylet assembly 119 and enable the return of information to the console 110, which may be used to determine the physical state associated with the stylet 120 along with monitored electrical signals such as ECG signaling via an electrical signaling logic 181 that supports receipt and processing of the received electrical signals from the stylet 120 (e.g., ports, analog-to-digital conversion logic, etc.). The physical state of the stylet 120 may be based on changes in characteristics of the reflected light signals 150 received at the console 110 from the stylet 120. The characteristics may include shifts in wavelength caused by strain on certain regions of the core fibers integrated within an optical fiber core 135 positioned within or operating as the stylet 120, as shown below. As discussed herein, the optical fiber core 135 may be comprised of core fibers $137_1$-$137_M$ (M=1 for a single core, and M≥2 for a multi-core), where the core fibers $137_1$-$137_M$ may collectively be referred to as core fiber(s) 137. Unless otherwise specified or the instant embodiment requires an alternative interpretation, embodiments discussed herein will refer to a multi-core optical fiber 135. From information associated with the reflected light signals 150, the console 110 may determine (through computation or extrapolation of the wavelength shifts) the physical state of the stylet 120, and also that of the catheter 195 configured to receive the stylet 120.

According to one embodiment of the disclosure, as shown in FIG. 1A, the optical logic 180 may include a light source 182 and an optical receiver 184. The light source 182 is configured to transmit the incident light 155 (e.g., broadband) for propagation over the optical fiber(s) 147 included in the interconnect 145, which are optically connected to the multi-core optical fiber core 135 within the stylet 120. In one embodiment, the light source 182 is a tunable swept laser, although other suitable light sources can also be employed in addition to a laser, including semi-coherent light sources, LED light sources, etc.

The optical receiver 184 is configured to: (i) receive returned optical signals, namely reflected light signals 150 received from optical fiber-based reflective gratings (sensors) fabricated within each core fiber of the multi-core optical fiber 135 deployed within the stylet 120, and (ii) translate the reflected light signals 150 into reflection data (from repository 192), namely data in the form of electrical signals representative of the reflected light signals including wavelength shifts caused by strain. The reflected light signals 150 associated with different spectral widths may include reflected light signals 151 provided from sensors positioned in the center core fiber (reference) of the multi-core optical fiber 135 and reflected light signals 152 provided from sensors positioned in the periphery core fibers of the multi-core optical fiber 135, as described below. Herein, the optical receiver 184 may be implemented as a photodetector, such as a positive-intrinsic-negative "PIN" photodiode, avalanche photodiode, or the like.

As shown, both the light source 182 and the optical receiver 184 are operably connected to the processor 160, which governs their operation. Also, the optical receiver 184 is operably coupled to provide the reflection data (from repository 192) to the memory 165 for storage and processing by reflection data classification logic 190. The reflection data classification logic 190 may be configured to: (i) identify which core fibers pertain to which of the received reflection data (from repository 192) and (ii) segregate the reflection data stored with a repository 192 provided from reflected light signals 150 pertaining to similar regions of the stylet 120 or spectral widths into analysis groups. The reflection data for each analysis group is made available to shape sensing logic 194 for analytics.

According to one embodiment of the disclosure, the shape sensing logic 194 is configured to compare wavelength shifts measured by sensors deployed in each periphery core fiber at the same measurement region of the stylet 120 (or same spectral width) to the wavelength shift at a center core fiber of the multi-core optical fiber 135 positioned along central axis and operating as a neutral axis of bending. From these analytics, the shape sensing logic 194 may determine the shape the core fibers have taken in 3D space and may further determine the current physical state of the catheter 195 in 3D space for rendering on the display 170.

According to one embodiment of the disclosure, the shape sensing logic 194 may generate a rendering of the current physical state of the stylet 120 (and potentially the catheter 195), based on heuristics or run-time analytics. For example, the shape sensing logic 194 may be configured in accordance with machine-learning techniques to access a data store (library) with pre-stored data (e.g., images, etc.) pertaining to different regions of the stylet 120 (or catheter 195) in which reflected light from core fibers have previously experienced similar or identical wavelength shifts. From the pre-stored data, the current physical state of the stylet 120 (or catheter 195) may be rendered. Alternatively, as another example, the shape sensing logic 194 may be configured to determine, during run-time, changes in the physical state of each region of the multi-core optical fiber 135 based on at least: (i) resultant wavelength shifts experienced by different core fibers within the optical fiber 135, and (ii) the relationship of these wavelength shifts generated by sensors positioned along different periphery core fibers at the same cross-sectional region of the multi-core optical fiber 135 to the wavelength shift generated by a sensor of the center core fiber at the same cross-sectional region. It is contemplated that other processes and procedures may be performed to utilize the wavelength shifts as measured by sensors along each of the core fibers within the multi-core optical fiber 135 to render appropriate changes in the physical state of the stylet 120 (and/or catheter 195), especially to enable guidance of the stylet 120, when positioned at a distal tip of the catheter 195, within the vasculature of the patient and at a desired destination within the body.

The console 110 may further include electrical signaling logic 181, which is positioned to receive one or more electrical signals from the stylet 120. The stylet 120 is configured to support both optical connectivity as well as electrical connectivity. The electrical signaling logic 181 receives the electrical signals (e.g., ECG signals) from the stylet 120 via the conductive medium. The electrical signals may be processed by electrical signal logic 196, executed by the processor 160, to determine ECG waveforms for display.

Additionally, the console 110 includes a fluctuation logic 198 that is configured to analyze at least a subset of the wavelength shifts measured by sensors deployed in each of the core fibers 137. In particular, the fluctuation logic 198 is configured to analyze wavelength shifts measured by sensors of core fibers 137, where such corresponds to an analysis of the fluctuation of the distal tip of the stylet 120 (or "tip fluctuation analysis"). In some embodiments, the fluctuation logic 198 measures analyzes the wavelength shifts measured by sensors at a distal end of the core fibers 137. The tip fluctuation analysis includes at least a correlation of detected movements of the distal tip of the stylet 120 (or other medical device or instrument) with experiential knowledge comprising previously detected movements (fluctuations), and optionally, other current measurements such as ECG signals. The experiential knowledge may include previously detected movements in various locations within the vasculature (e.g., SVC, Inferior Vena Cava (IVC), right atrium, azygos vein, other blood vessels such as arteries and veins) under normal, healthy conditions and in the presence of defects (e.g., vessel constriction, vasospasm, vessel occlusion, etc.). Thus, the tip fluctuation analysis may result in a confirmation of tip location and/or detection of a defect affecting a blood vessel.

It should be noted that the fluctuation logic 198 need not perform the same analyses as the shape sensing logic 194. For instance, the shape sensing logic 194 determines a 3D shape of the stylet 120 by comparing wavelength shifts in outer core fibers of a multi-core optical fiber to a center, reference core fiber. The fluctuation logic 198 may instead correlate the wavelength shifts to previously measured wavelength shifts and optionally other current measurements without distinguishing between wavelength shifts of outer core fibers and a center, reference core fiber as the tip fluctuation analysis need not consider direction or shape within a 3D space.

In some embodiments, e.g., those directed at tip location confirmation, the analysis of the fluctuation logic 198 may utilize electrical signals (e.g., ECG signals) measured by the electrical signaling logic 181. For example, the fluctuation logic 198 may compare the movements of a subsection of the stylet 120 (e.g., the distal tip) with electrical signals indicating impulses of the heart (e.g., the heartbeat). Such a comparison may reveal whether the distal tip is within the SVC or the right atrium based on how closely the movements correspond to a rhythmic heartbeat.

In various embodiments, a display and/or alert may be generated based on the fluctuation analysis. For instance, the fluctuation logic 198 may generate a graphic illustrating the detected fluctuation compared to previously detected tip fluctuations and/or the anatomical movements of the patient body such as rhythmic pulses of the heart and/or expanding and contracting of the lungs. In one embodiment, such a graphic may include a dynamic visualization of the present medical device moving in accordance with the detected fluctuations adjacent to a secondary medical device moving in accordance with previously detected tip fluctuations. In some embodiments, the location of a subsection of the medical device may be obtained from the shape sensing logic 194 and the dynamic visualization may be location-specific (e.g., such that the previously detected fluctuations illustrate expected fluctuations for the current location of the subsection). In alternative embodiments, the dynamic visualization may illustrate a comparison of the dynamic movements of the subsection to one or more subsections moving in accordance with previously detected fluctuations of one or more defects affecting the blood vessel.

According to one embodiment of the disclosure, the fluctuation logic 198 may determine whether movements of one or more subsections of the stylet 120 indicate a location of a particular subsection of the stylet 120 or a defect affecting a blood vessel and, as a result, of the catheter 195, based on heuristics or run-time analytics. For example, the fluctuation logic 198 may be configured in accordance with machine-learning techniques to access a data store (library) with pre-stored data (e.g., experiential knowledge of previously detected tip fluctuation data, etc.) pertaining to different regions (subsections) of the stylet 120. Specifically, such an embodiment may include processing of a machine-learning model trained using the experiential knowledge, where the detected fluctuations serve as input to the trained model and processing of the trained model results in a determination as to how closely the detected fluctuations correlate to one or more locations within the vasculature of the patient and/or one or more defects affecting a blood vessel.

In some embodiments, the fluctuation logic 198 may be configured to determine, during run-time, whether movements of one or more subsections of the stylet 120 (and the catheter 195) indicate a location of a particular subsection of the stylet 120 or a defect affecting a blood vessel, based on at least (i) resultant wavelength shifts experienced by the core fibers 137 within the one or more subsections, and (ii) the correlation of these wavelength shifts generated by sensors positioned along different core fibers at the same cross-sectional region of the stylet 120 (or the catheter 195) to previously detected wavelength shifts generated by corresponding sensors in a core fiber at the same cross-sectional region. It is contemplated that other processes and procedures may be performed to utilize the wavelength shifts as measured by sensors along each of the core fibers 137 to render appropriate movements in the distal tip of the stylet 120 and/or the catheter 195.

Figure 1B:
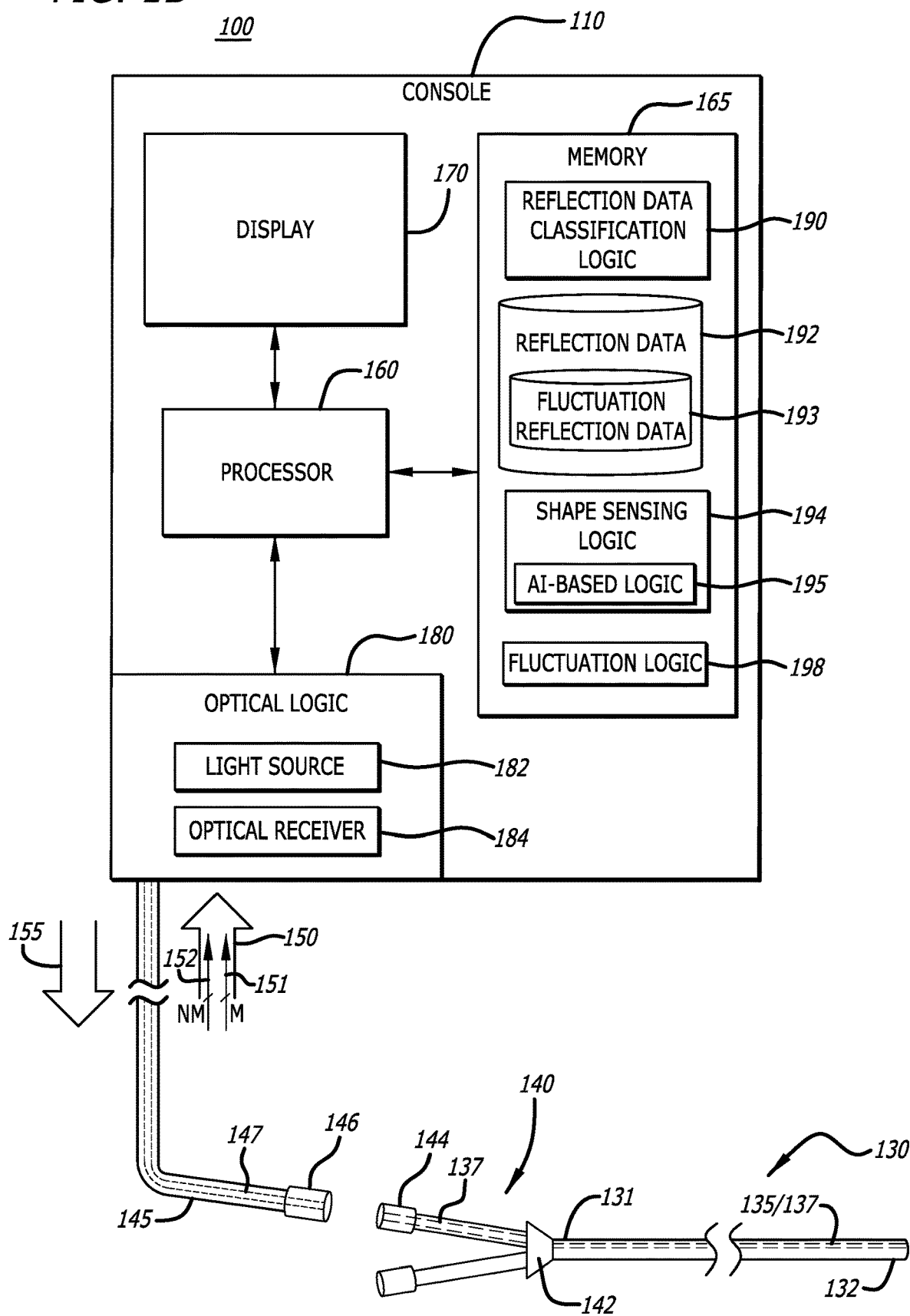
FIG. 1B is an alternative illustrative embodiment of the medical instrument monitoring system 100 in accordance with some embodiments.

Referring to FIG. 1B, an alternative exemplary embodiment of a medical instrument monitoring system 100 is shown. Herein, the medical instrument monitoring system 100 features a console 110 and a medical instrument 130 communicatively coupled to the console 110. For this embodiment, the medical instrument 130 corresponds to a catheter, which features an integrated tubing with two or more lumen extending between a proximal end 131 and a distal end 132 of the integrated tubing. The integrated tubing (sometimes referred to as "catheter tubing") is in communication with one or more extension legs 140 via a bifurcation hub 142. An optical-based catheter connector 144 may be included on a proximal end of at least one of the extension legs 140 to enable the catheter 130 to operably connect to the console 110 via an interconnect 145 or another suitable component. Herein, the interconnect 145 may include a connector 146 that, when coupled to the optical-based catheter connector 144, establishes optical connectivity between one or more optical fibers 147 (hereinafter, "optical fiber(s)") included as part of the interconnect 145 and core fibers 137 deployed within the catheter 130 and integrated into the tubing. Alternatively, a different combination of connectors, including one or more adapters, may be used to optically connect the optical fiber(s) 147 to the core fibers 137 within the catheter 130. The core fibers 137 deployed within the catheter 130 as illustrated in FIG. 1B include the same characteristics and perform the same functionalities as the core fibers 137 deployed within the stylet 120 of FIG. 1A.

The optical logic 180 is configured to support graphical rendering of the catheter 130, most notably the integrated tubing of the catheter 130, based on characteristics of the reflected light signals 150 received from the catheter 130. The characteristics may include shifts in wavelength caused by strain on certain regions of the core fibers 137 integrated within (or along) a wall of the integrated tubing, which may be used to determine (through computation or extrapolation of the wavelength shifts) the physical state of the catheter 130, notably its integrated tubing or a portion of the integrated tubing such as a tip or distal end of the tubing to read fluctuations (real-time movement) of the tip (or distal end).

More specifically, the optical logic 180 includes a light source 182. The light source 182 is configured to transmit the broadband incident light 155 for propagation over the optical fiber(s) 147 included in the interconnect 145, which are optically connected to multiple core fibers 137 within the catheter tubing. Herein, the optical receiver 184 is configured to: (i) receive returned optical signals, namely reflected light signals 150 received from optical fiber-based reflective gratings (sensors) fabricated within each of the core fibers 137 deployed within the catheter 130, and (ii) translate the reflected light signals 150 into reflection data (from repository 192), namely data in the form of electrical signals representative of the reflected light signals including wavelength shifts caused by strain. The reflected light signals 150 associated with different spectral widths include reflected light signals 151 provided from sensors positioned in the center core fiber (reference) of the catheter 130 and reflected light signals 152 provided from sensors positioned in the outer core fibers of the catheter 130, as described below.

As noted above, the shape sensing logic 194 is configured to compare wavelength shifts measured by sensors deployed in each outer core fiber at the same measurement region of the catheter (or same spectral width) to the wavelength shift at the center core fiber positioned along central axis and operating as a neutral axis of bending. From these analytics, the shape sensing logic 190 may determine the shape the core fibers have taken in 3D space and may further determine the current physical state of the catheter 130 in 3D space for rendering on the display 170.

According to one embodiment of the disclosure, the shape sensing logic 194 may generate a rendering of the current physical state of the catheter 130, especially the integrated tubing, based on heuristics or run-time analytics. For example, the shape sensing logic 194 may be configured in accordance with machine-learning techniques to access a data store (library) with pre-stored data (e.g., images, etc.) pertaining to different regions of the catheter 130 in which the core fibers 137 experienced similar or identical wavelength shifts. From the pre-stored data, the current physical state of the catheter 130 may be rendered. Alternatively, as another example, the shape sensing logic 194 may be configured to determine, during run-time, changes in the physical state of each region of the catheter 130, notably the tubing, based on at least (i) resultant wavelength shifts experienced by the core fibers 137 and (ii) the relationship of these wavelength shifts generated by sensors positioned along different outer core fibers at the same cross-sectional region of the catheter 130 to the wavelength shift generated by a sensor of the center core fiber at the same cross-sectional region. It is contemplated that other processes and procedures may be performed to utilize the wavelength shifts as measured by sensors along each of the core fibers 137 to render appropriate changes in the physical state of the catheter 130.

Figure 2:
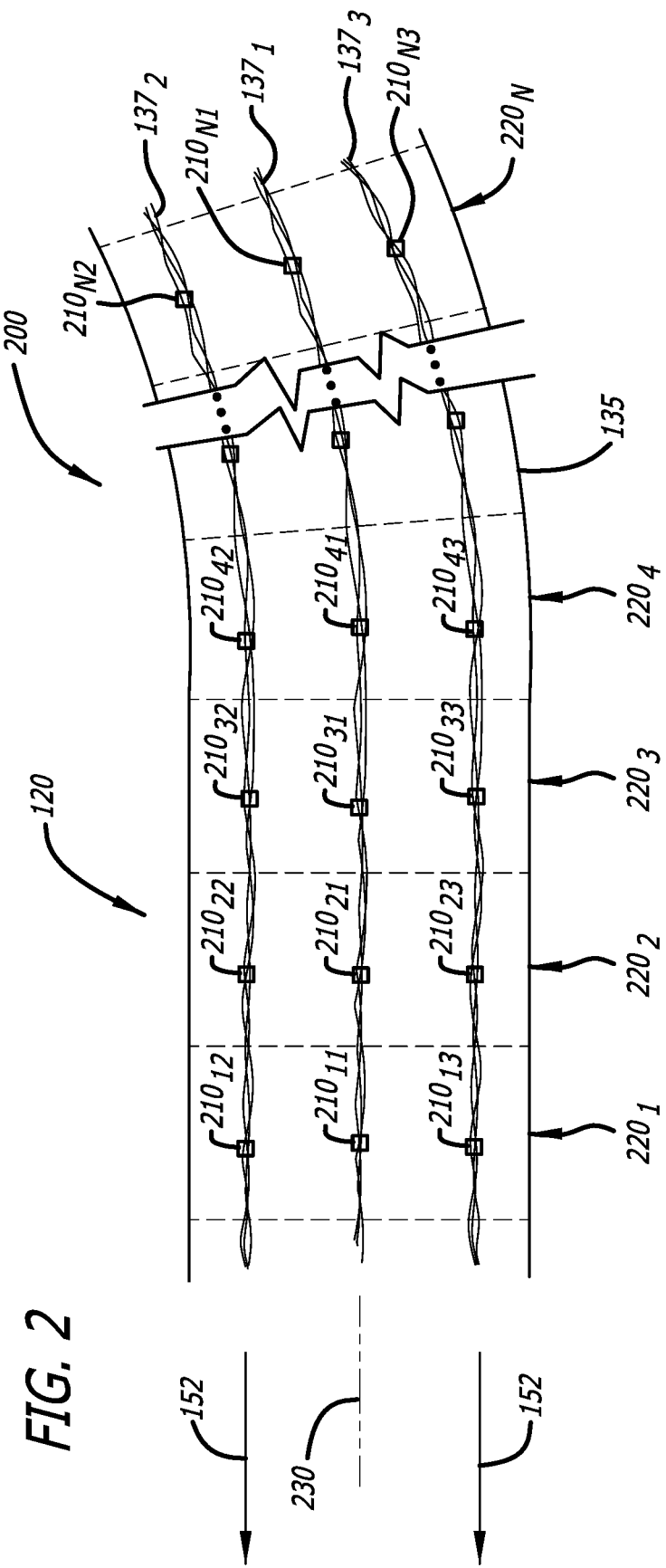
FIG. 2 is an exemplary embodiment of a structure of a section of the multi-core optical fiber included within the stylet 120 of FIG. 1A in accordance with some embodiments.

Referring to FIG. 2, an exemplary embodiment of a structure of a section of the multi-core optical fiber included within the stylet 120 of FIG. 1A is shown in accordance with some embodiments. The multi-core optical fiber section 200 of the multi-core optical fiber 135 depicts certain core fibers $137_1$-$137_M$ (M≥2, M=4 as shown, see FIG. 3A) along with the spatial relationship between sensors (e.g., reflective gratings) $210_{11}$-$210_{NM}$ (N≥2; M≥2) present within the core fibers $137_1$-$137_M$, respectively. As noted above, the core fibers $137_1$-$137_M$ may be collectively referred to as "the core fibers 137."

As shown, the section 200 is subdivided into a plurality of cross-sectional regions $220_1$-$220_N$, where each cross-sectional region $220_1$-$220_N$ corresponds to reflective gratings $210_{11}$-$210_{14}$ . . . $210_{N1}$-$210_{N4}$. Some or all of the cross-sectional regions $220_1$ . . . $220_N$ may be static (e.g., prescribed length) or may be dynamic (e.g., vary in size among the regions $220_1$ . . . $220_N$). A first core fiber $137_1$ is positioned substantially along a center (neutral) axis 230 while core fiber $137_2$ may be oriented within the cladding of the multi-core optical fiber 135, from a cross-sectional, front-facing perspective, to be position on "top" the first core fiber $137_1$. In this deployment, the core fibers $137_3$ and $137_4$ may be positioned "bottom left" and "bottom right" of the first core fiber $137_1$. As examples, FIGS. 3A-4B provides illustrations of such.

Referencing the first core fiber $137_1$ as an illustrative example, when the stylet 120 is operative, each of the reflective gratings $210_1$-$210_N$ reflects light for a different spectral width. As shown, each of the gratings $210_{1i}$-$210_{Ni}$ (1≤i≤M) is associated with a different, specific spectral width, which would be represented by different center frequencies of $f_1$ . . . $f_N$, where neighboring spectral widths reflected by neighboring gratings are non-overlapping according to one embodiment of the disclosure.

Herein, positioned in different core fibers $137_2$-$137_3$ but along at the same cross-sectional regions $220$-$220_N$ of the multi-core optical fiber 135, the gratings $210_{12}$-$210_{N2}$ and $210_{13}$-$210_{N3}$ are configured to reflect incoming light at same (or substantially similar) center frequency. As a result, the reflected light returns information that allows for a determination of the physical state of the optical fibers 137 (and the stylet 120) based on wavelength shifts measured from the returned, reflected light. In particular, strain (e.g., compression or tension) applied to the multi-core optical fiber 135 (e.g., at least core fibers $137_2$-$137_3$) results in wavelength shifts associated with the returned, reflected light. Based on different locations, the core fibers $137_1$-$137_4$ experience different types and degree of strain based on angular path changes as the stylet 120 advances in the patient.

For example, with respect to the multi-core optical fiber section 200 of FIG. 2, in response to angular (e.g., radial) movement of the stylet 120 is in the left-veering direction, the fourth core fiber $137_4$ (see FIG. 3A) of the multi-core optical fiber 135 with the shortest radius during movement (e.g., core fiber closest to a direction of angular change) would exhibit compression (e.g., forces to shorten length). At the same time, the third core fiber $137_3$ with the longest radius during movement (e.g., core fiber furthest from the direction of angular change) would exhibit tension (e.g., forces to increase length). As these forces are different and unequal, the reflected light from reflective gratings $210_{N2}$ and $210_{N3}$ associated with the core fiber $137_2$ and $137_3$ will exhibit different changes in wavelength. The differences in wavelength shift of the reflected light signals 150 can be used to extrapolate the physical configuration of the stylet 120 by determining the degrees of wavelength change caused by compression/tension for each of the periphery fibers (e.g., the second core fiber $137_2$ and the third core fiber $137_3$) in comparison to the wavelength of the reference core fiber (e.g., first core fiber $137_1$) located along the neutral axis 230 of the multi-core optical fiber 135. These degrees of wavelength change may be used to extrapolate the physical state of the stylet 120. The reflected light signals 150 are reflected back to the console 110 via individual paths over a particular core fiber $137_1$-$137_M$.

Referring to FIG. 3A, a first exemplary embodiment of the stylet of FIG. 1A supporting both an optical and electrical signaling is shown in accordance with some embodiments. Herein, the stylet 120 features a centrally located multi-core optical fiber 135, which includes a cladding 300 and a plurality of core fibers $137_1$-$137_M$ (M≥2; M=4) residing within a corresponding plurality of lumens $320_1$-$320_M$. While the multi-core optical fiber 135 is illustrated within four (4) core fibers $137_1$-$137_4$, a greater number of core fibers $137_1$-$137_M$ (M>4) may be deployed to provide a more detailed three-dimensional sensing of the physical state (e.g., shape, etc.) of the multi-core optical fiber 135 and the stylet 120 deploying the optical fiber 135.

For this embodiment of the disclosure, the multi-core optical fiber 135 is encapsulated within a concentric braided tubing 310 positioned over a low coefficient of friction layer 335. The braided tubing 310 may feature a "mesh" construction, in which the spacing between the intersecting conductive elements is selected based on the degree of rigidity desired for the stylet 120, as a greater spacing may provide a lesser rigidity, and thereby, a more pliable stylet 120.

According to this embodiment of the disclosure, as shown in FIGS. 3A-3B, the core fibers $137_1$-$137_4$ include (i) a central core fiber $137_1$ and (ii) a plurality of periphery core fibers $137_2$-$137_4$, which are maintained within lumens $320_1$-$320_4$ formed in the cladding 300. According to one embodiment of the disclosure, one or more of the lumen $320_1$-$320_4$ may be configured with a diameter sized to be greater than the diameter of the core fibers $137_1$-$137_4$. By avoiding a majority of the surface area of the core fibers $137_1$-$137_4$ from being in direct physical contact with a wall surface of the lumens $320_1$-$320_4$, the wavelength changes to the incident light are caused by angular deviations in the multi-core optical fiber 135 thereby reducing influence of compression and tension forces being applied to the walls of the lumens $320_1$-$320_M$, not the core fibers $137_1$-$137_M$ themselves.

As further shown in FIGS. 3A-3B, the core fibers $137_1$-$137_4$ may include central core fiber $137_1$ residing within a first lumen $320_1$ formed along the first neutral axis 230 and a plurality of core fibers $137_2$-$137_4$ residing within lumens $320_2$-$320_4$ each formed within different areas of the cladding 300 radiating from the first neutral axis 230. In general, the core fibers $137_2$-$137_4$, exclusive of the central core fiber $137_1$, may be positioned at different areas within a cross-sectional area 305 of the cladding 300 to provide sufficient separation to enable three-dimensional sensing of the multi-core optical fiber 135 based on changes in wavelength of incident light propagating through the core fibers $137_2$-$137_4$ and reflected back to the console for analysis.

For example, where the cladding 300 features a circular cross-sectional area 305 as shown in FIG. 3B, the core fibers $137_2$-$137_4$ may be positioned substantially equidistant from each other as measured along a perimeter of the cladding 300, such as at "top" (12 o'clock), "bottom-left" (8 o'clock) and "bottom-right" (4 o'clock) locations as shown. Hence, in general terms, the core fibers $137_2$-$137_4$ may be positioned within different segments of the cross-sectional area 305. Where the cross-sectional area 305 of the cladding 300 has a distal tip 330 and features a polygon cross-sectional shape (e.g., triangular, square, rectangular, pentagon, hexagon, octagon, etc.), the central core fiber $137_1$ may be located at or near a center of the polygon shape, while the remaining core fibers $137_2$-$137_M$ may be located proximate to angles between intersecting sides of the polygon shape.

Referring still to FIGS. 3A-3B, operating as the conductive medium for the stylet 120, the braided tubing 310 provides mechanical integrity to the multi-core optical fiber 135 and operates as a conductive pathway for electrical signals. For example, the braided tubing 310 may be exposed to a distal tip of the stylet 120. The cladding 300 and the braided tubing 310, which is positioned concentrically surrounding a circumference of the cladding 300, are contained within the same insulating layer 350. The insulating layer 350 may be a sheath or conduit made of protective, insulating (e.g., non-conductive) material that encapsulates both for the cladding 300 and the braided tubing 310, as shown.

Referring to FIG. 4A, a second exemplary embodiment of the stylet of FIG. 1B is shown in accordance with some embodiments. Referring now to FIG. 4A, a second exemplary embodiment of the stylet 120 of FIG. 1B supporting both an optical and electrical signaling is shown. Herein, the stylet 120 features the multi-core optical fiber 135 described above and shown in FIG. 3A, which includes the cladding 300 and the first plurality of core fibers $137_1$-$137_M$ (M≥3; M=4 for embodiment) residing within the corresponding plurality of lumens $320_1$-$320_M$. For this embodiment of the disclosure, the multi-core optical fiber 135 includes the central core fiber $137_1$ residing within the first lumen $320_1$ formed along the first neutral axis 230 and the second plurality of core fibers $137_2$-$137_4$ residing within corresponding lumens $320_2$-$320_4$ positioned in different segments within the cross-sectional area 305 of the cladding 300. Herein, the multi-core optical fiber 135 is encapsulated within a conductive tubing 400. The conductive tubing 400 may feature a "hollow" conductive cylindrical member concentrically encapsulating the multi-core optical fiber 135.

Referring to FIGS. 4A-4B, operating as a conductive medium for the stylet 120 in the transfer of electrical signals (e.g., ECG signals) to the console, the conductive tubing 400 may be exposed up to a tip 410 of the stylet 120. For this embodiment of the disclosure, a conductive epoxy 420 (e.g., metal-based epoxy such as a silver epoxy) may be affixed to the tip 410 and similarly joined with a termination/connection point created at a proximal end 430 of the stylet 120. The cladding 300 and the conductive tubing 400, which is positioned concentrically surrounding a circumference of the cladding 300, are contained within the same insulating layer 440. The insulating layer 440 may be a protective conduit encapsulating both for the cladding 300 and the conductive tubing 400, as shown.

Figure 5A:
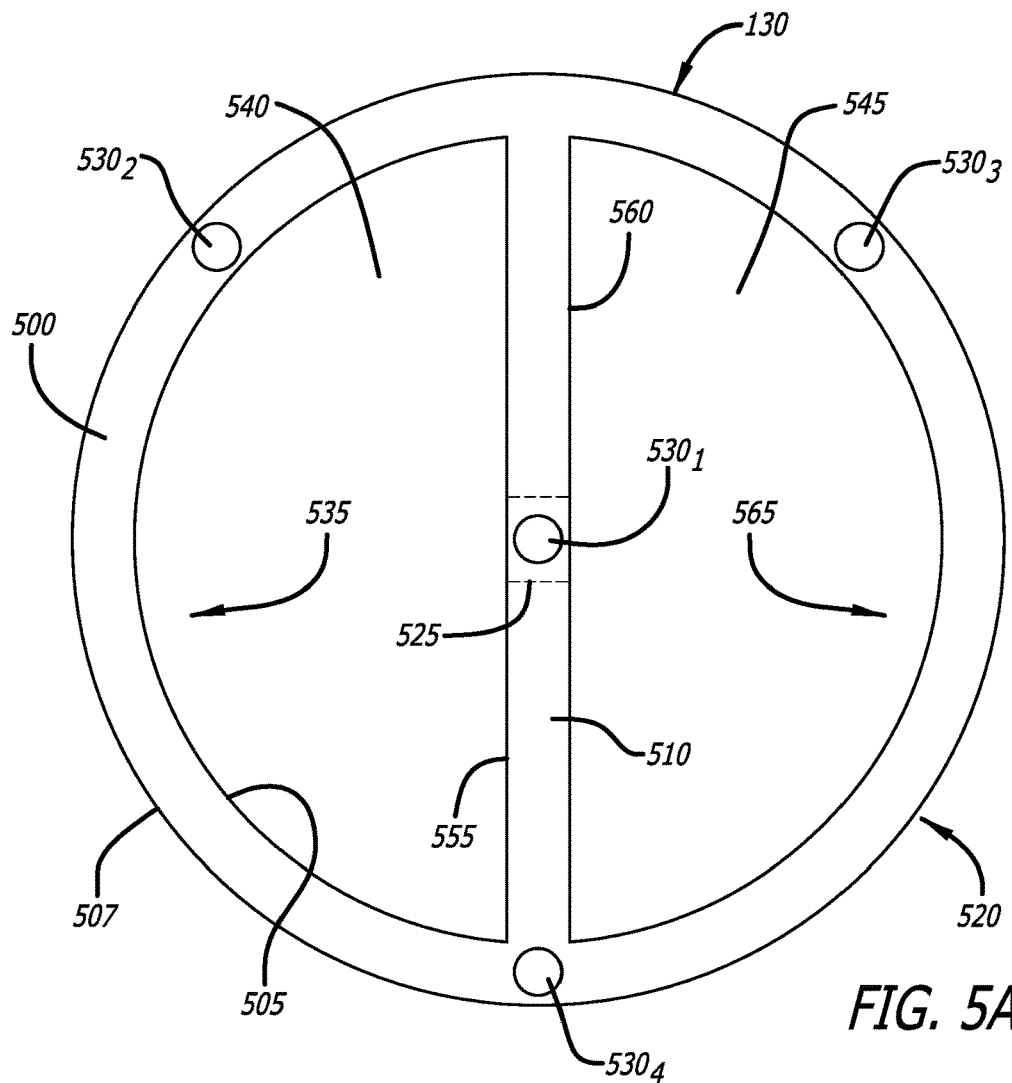
FIG. 5A is an elevation view of a first illustrative embodiment of a catheter including integrated tubing, a diametrically disposed septum, and micro-lumens formed within the tubing and septum in accordance with some embodiments.

Referring to FIG. 5A, an elevation view of a first illustrative embodiment of a catheter including integrated tubing, a diametrically disposed septum, and micro-lumens formed within the tubing and septum is shown in accordance with some embodiments. Herein, the catheter 130 includes integrated tubing, the diametrically disposed septum 510, and the plurality of micro-lumens $530_1$-$530_4$ which, for this embodiment, are fabricated to reside within the wall 500 of the integrated tubing of the catheter 130 and within the septum 510. In particular, the septum 510 separates a single lumen, formed by the inner surface 505 of the wall 500 of the catheter 130, into multiple lumen, namely two lumens 540 and 545 as shown. Herein, the first lumen 540 is formed between a first arc-shaped portion 535 of the inner surface 505 of the wall 500 forming the catheter 130 and a first outer surface 555 of the septum 510 extending longitudinally within the catheter 130. The second lumen 545 is formed between a second arc-shaped portion 565 of the inner surface 505 of the wall 500 forming the catheter 130 and a second outer surfaces 560 of the septum 510.

According to one embodiment of the disclosure, the two lumens 540 and 545 have approximately the same volume. However, the septum 510 need not separate the tubing into two equal lumens. For example, instead of the septum 510 extending vertically (12 o'clock to 6 o'clock) from a front-facing, cross-sectional perspective of the tubing, the septum 510 could extend horizontally (3 o'clock to 9 o'clock), diagonally (1 o'clock to 7 o'clock; 10 o'clock to 4 o'clock) or angularly (2 o'clock to 10 o'clock). In the later configuration, each of the lumens 540 and 545 of the catheter 130 would have a different volume.

With respect to the plurality of micro-lumens $530_1$-$530_4$, the first micro-lumen $530_1$ is fabricated within the septum 510 at or near the cross-sectional center 525 of the integrated tubing. For this embodiment, three micro-lumens $530_2$-$530_4$ are fabricated to reside within the wall 500 of the catheter 130. In particular, a second micro-lumen $530_2$ is fabricated within the wall 500 of the catheter 130, namely between the inner surface 505 and outer surface 507 of the first arc-shaped portion 535 of the wall 500. Similarly, the third micro-lumen $530_3$ is also fabricated within the wall 500 of the catheter 130, namely between the inner and outer surfaces 505/507 of the second arc-shaped portion 555 of the wall 500. The fourth micro-lumen $530_4$ is also fabricated within the inner and outer surfaces 505/507 of the wall 500 that are aligned with the septum 510.

According to one embodiment of the disclosure, as shown in FIG. 5A, the micro-lumens $530_2$-$530_4$ are positioned in accordance with a "top-left" (10 o'clock), "top-right" (2 o'clock) and "bottom" (6 o'clock) layout from a front-facing, cross-sectional perspective. Of course, the micro-lumens $530_2$-$530_4$ may be positioned differently, provided that the micro-lumens $530_2$-$530_4$ are spatially separated along the circumference 520 of the catheter 130 to ensure a more robust collection of reflected light signals from the outer core fibers $570_2$-$570_4$ when installed. For example, two or more of micro-lumens (e.g., micro-lumens $530_2$ and $530_4$) may be positioned at different quadrants along the circumference 520 of the catheter wall 500.

Figure 5B:
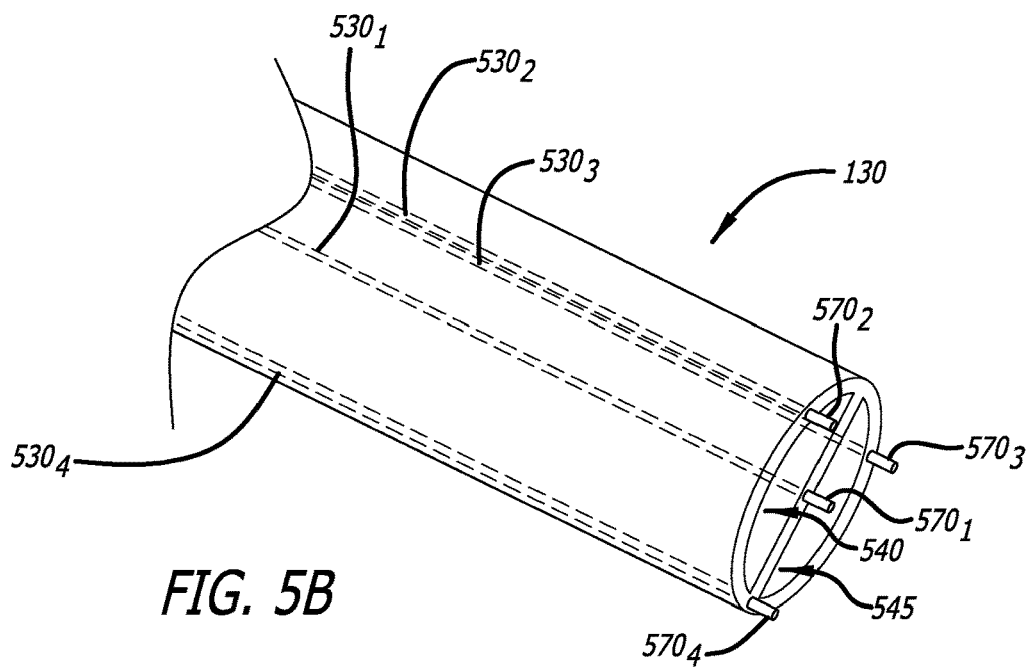
FIG. 5B is a perspective view of the first illustrative embodiment of the catheter of FIG. 5A including core fibers installed within the micro-lumens in accordance with some embodiments.

Referring to FIG. 5B, a perspective view of the first illustrative embodiment of the catheter of FIG. 5A including core fibers installed within the micro-lumens is shown in accordance with some embodiments. According to one embodiment of the disclosure, the second plurality of micro-lumens $530_2$-$530_4$ are sized to retain corresponding outer core fibers $570_2$-$570_4$, where the diameter of each of the second plurality of micro-lumens $530_2$-$530_4$ may be sized just larger than the diameters of the outer core fibers $570_2$-$570_4$. The size differences between a diameter of a single core fiber and a diameter of any of the micro-lumen $530_1$-$530_4$ may range between 0.001 micrometers (μm) and 1000 μm, for example. As a result, the cross-sectional areas of the outer core fibers $570_2$-$570_4$ would be less than the cross-sectional areas of the corresponding micro-lumens $530_2$-$530_4$. A "larger" micro-lumen (e.g., micro-lumen $530_2$) may better isolate external strain being applied to the outer core fiber $570_2$ from strain directly applied to the catheter 130 itself. Similarly, the first micro-lumen $530_1$ may be sized to retain the center core fiber $570_1$, where the diameter of the first micro-lumen $530_1$ may be sized just larger than the diameter of the center core fiber $570_1$.

As an alternative embodiment of the disclosure, one or more of the micro-lumens $530_1$-$530_4$ may be sized with a diameter that exceeds the diameter of the corresponding one or more core fibers $570_1$-$570_4$. However, at least one of the micro-lumens $530_1$-$530_4$ is sized to fixedly retain their corresponding core fiber (e.g., core fiber retained with no spacing between its lateral surface and the interior wall surface of its corresponding micro-lumen). As yet another alternative embodiment of the disclosure, all the micro-lumens $530_1$-$530_4$ are sized with a diameter to fixedly retain the core fibers $570_1$-$570_4$.

Figure 6A:
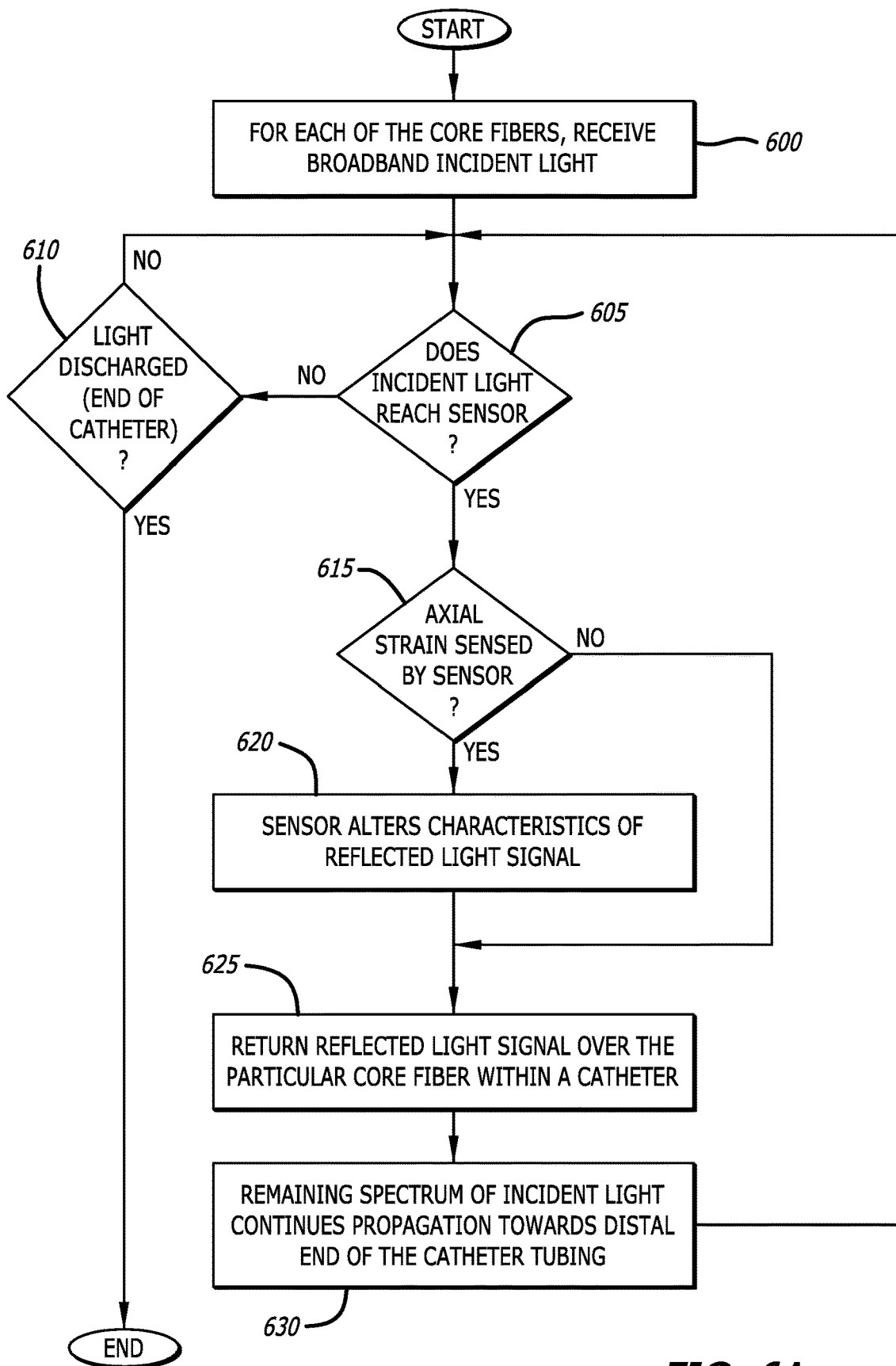
FIGS. 6A-6B are flowcharts of the methods of operations conducted by the medical instrument monitoring system of FIGS. 1A-1B to achieve optic 3D shape sensing in accordance with some embodiments.
Figure 6B:
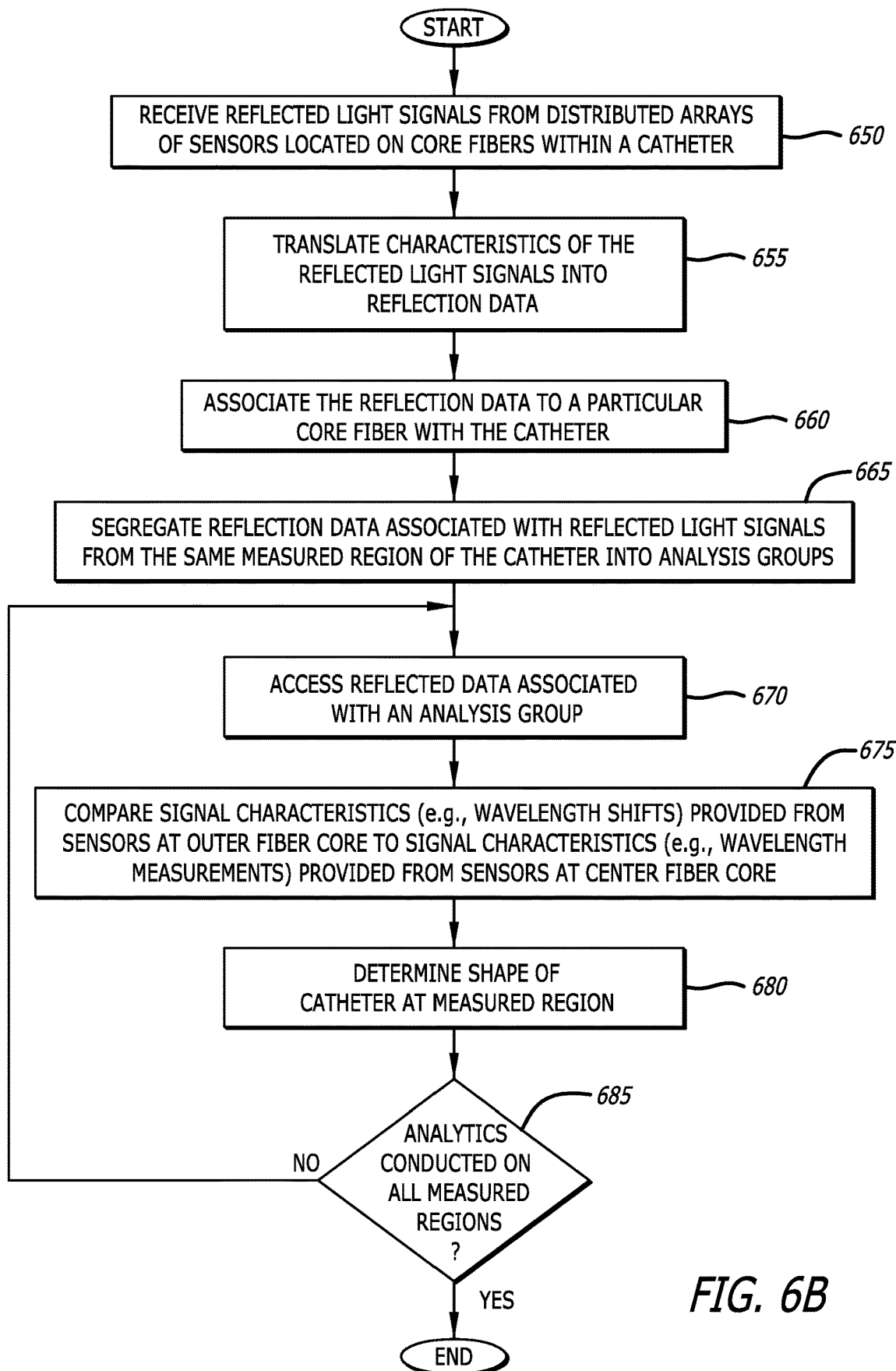

Referring to FIGS. 6A-6B, flowcharts of methods of operations conducted by the medical instrument monitoring system of FIGS. 1A-1B to achieve optic 3D shape sensing are shown in accordance with some embodiments. Herein, the catheter includes at least one septum spanning across a diameter of the tubing wall and continuing longitudinally to subdivide the tubing wall. The medial portion of the septum is fabricated with a first micro-lumen, where the first micro-lumen is coaxial with the central axis of the catheter tubing. The first micro-lumen is configured to retain a center core fiber. Two or more micro-lumen, other than the first micro-lumen, are positioned at different locations circumferentially spaced along the wall of the catheter tubing. For example, two or more of the second plurality of micro-lumens may be positioned at different quadrants along the circumference of the catheter wall.

Furthermore, each core fiber includes a plurality of sensors spatially distributed along its length between at least the proximal and distal ends of the catheter tubing. This array of sensors is distributed to position sensors at different regions of the core fiber to enable distributed measurements of strain throughout the entire length or a selected portion of the catheter tubing. These distributed measurements may be conveyed through reflected light of different spectral widths (e.g., specific wavelength or specific wavelength ranges) that undergoes certain wavelength shifts based on the type and degree of strain.

According to one embodiment of the disclosure, as shown in FIG. 6A, for each core fiber, broadband incident light is supplied to propagate through a particular core fiber (block 600). Unless discharged, upon the incident light reaching a sensor of a distributed array of sensors measuring strain on a particular core fiber, light of a prescribed spectral width associated with the first sensor is to be reflected back to an optical receiver within a console (blocks 605-610). Herein, the sensor alters characteristics of the reflected light signal to identify the type and degree of strain on the particular core fiber as measured by the first sensor (blocks 615-620). According to one embodiment of the disclosure, the alteration in characteristics of the reflected light signal may signify a change (shift) in the wavelength of the reflected light signal from the wavelength of the incident light signal associated with the prescribed spectral width. The sensor returns the reflected light signal over the core fiber and the remaining spectrum of the incident light continues propagation through the core fiber toward a distal end of the catheter tubing (blocks 625-630). The remaining spectrum of the incident light may encounter other sensors of the distributed array of sensors, where each of these sensors would operate as set forth in blocks 605-630 until the last sensor of the distributed array of sensors returns the reflected light signal associated with its assigned spectral width and the remaining spectrum is discharged as illumination.

Referring now to FIG. 6B, during operation, multiple reflected light signals are returned to the console from each of the plurality of core fibers residing within the corresponding plurality of micro-lumens formed within a catheter, such as the catheter of FIG. 1B. In particular, the optical receiver receives reflected light signals from the distributed arrays of sensors located on the center core fiber and the outer core fibers and translates the reflected light signals into reflection data, namely electrical signals representative of the reflected light signals including wavelength shifts caused by strain (blocks 650-655). The reflection data classification logic is configured to identify which core fibers pertain to which reflection data and segregate reflection data provided from reflected light signals pertaining to a particular measurement region (or similar spectral width) into analysis groups (block 660-665).

Each analysis group of reflection data is provided to shape sensing logic for analytics (block 670). Herein, the shape sensing logic compares wavelength shifts at each outer core fiber with the wavelength shift at the center core fiber positioned along central axis and operating as a neutral axis of bending (block 675). From this analytics, on all analytic groups (e.g., reflected light signals from sensors in all or most of the core fibers), the shape sensing logic may determine the shape the core fibers have taken in three-dimensional space, from which the shape sensing logic can determine the current physical state of the catheter in three-dimension space (blocks 680-685).

Figure 7:
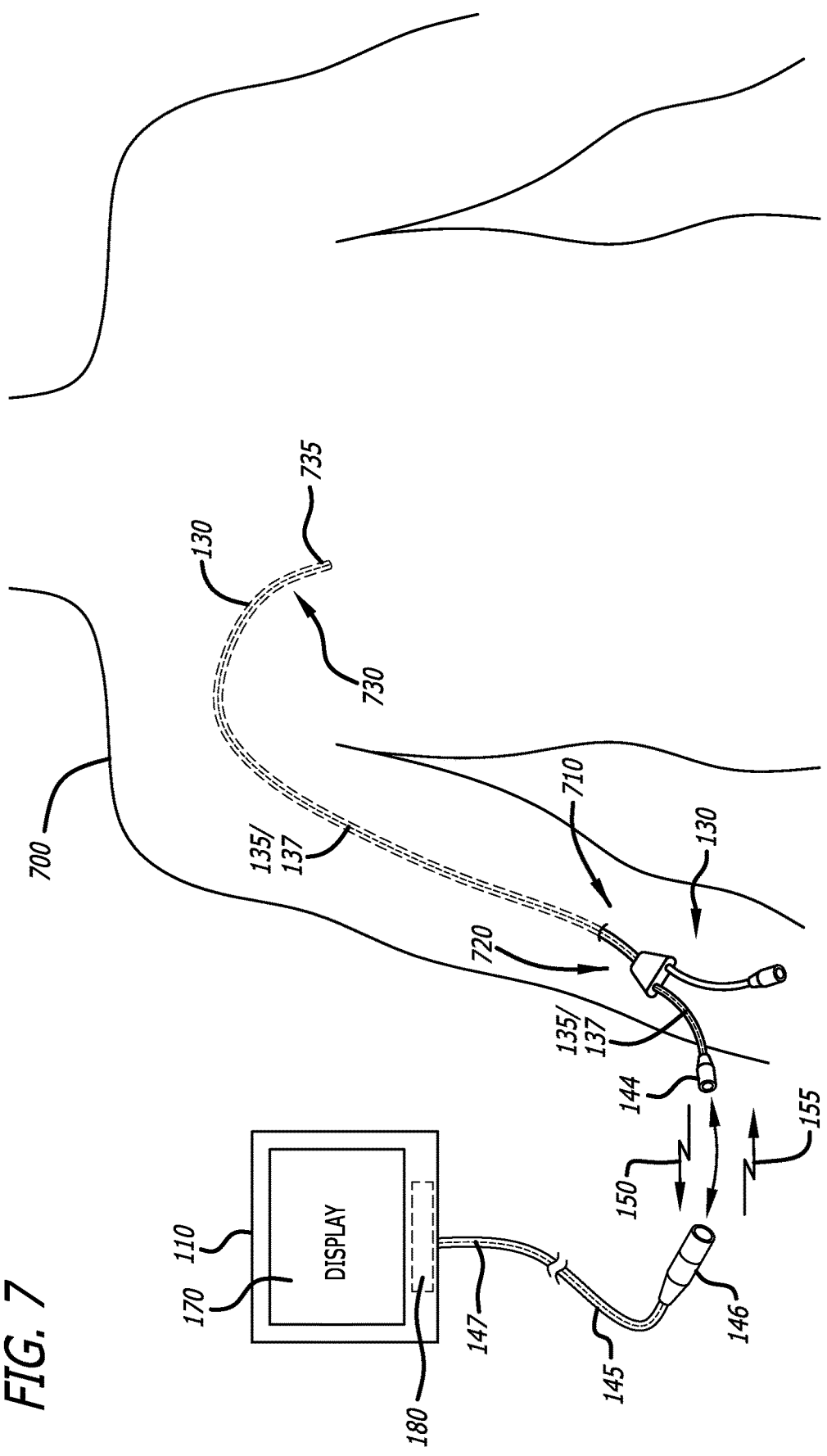
FIG. 7 is an exemplary embodiment of the medical instrument monitoring system of FIG. 1B during operation and insertion of the catheter into a patient in accordance with some embodiments.

Referring to FIG. 7, an exemplary embodiment of the medical instrument monitoring system of FIG. 1B during operation and insertion of the catheter into a patient are shown in accordance with some embodiments. Herein, the catheter 130 generally includes the integrated tubing of the catheter 130 with a proximal portion 720 that generally remains exterior to the patient 700 and a distal portion 730 that generally resides within the patient vasculature after placement is complete. The (integrated) catheter tubing of the catheter 130 may be advanced to a desired position within the patient vasculature such as a distal end (or tip) 735 of the catheter tubing of the catheter 130 is proximate the patient's heart, such as in the lower one-third (⅓) portion of the Superior Vena Cava ("SVC") for example. In some embodiments, various instruments may be disposed at the distal end 735 of the catheter 130 to measure pressure of blood in a certain heart chamber and in the blood vessels, view an interior of blood vessels, or the like. In alternative embodiments, such as those that utilize the stylet assembly of FIG. 1A and the catheter 195, such instruments may be disposed at a distal end of the stylet 120.

During advancement through a patient vasculature, the catheter tubing of the catheter 130 receives broadband incident light 155 from the console 110 via optical fiber(s) 147 within the interconnect 145, where the incident light 155 propagates along the core fibers 137 of the multi-core optical fiber 135 within the catheter tubing of the catheter 130. According to one embodiment of the disclosure, the connector 146 of the interconnect 145 terminating the optical fiber(s) 147 may be coupled to the optical-based catheter connector 144, which may be configured to terminate the core fibers 137 deployed within the catheter 130. Such coupling optically connects the core fibers 137 of the catheter 130 with the optical fiber(s) 147 within the interconnect 145. The optical connectivity is needed to propagate the incident light 155 to the core fibers 137 and return the reflected light signals 150 to the optical logic 180 within the console 110 over the interconnect 145. As described below in detail, the physical state of the catheter 130 may be ascertained based on analytics of the wavelength shifts of the reflected light signals 150.

Figure 8A:
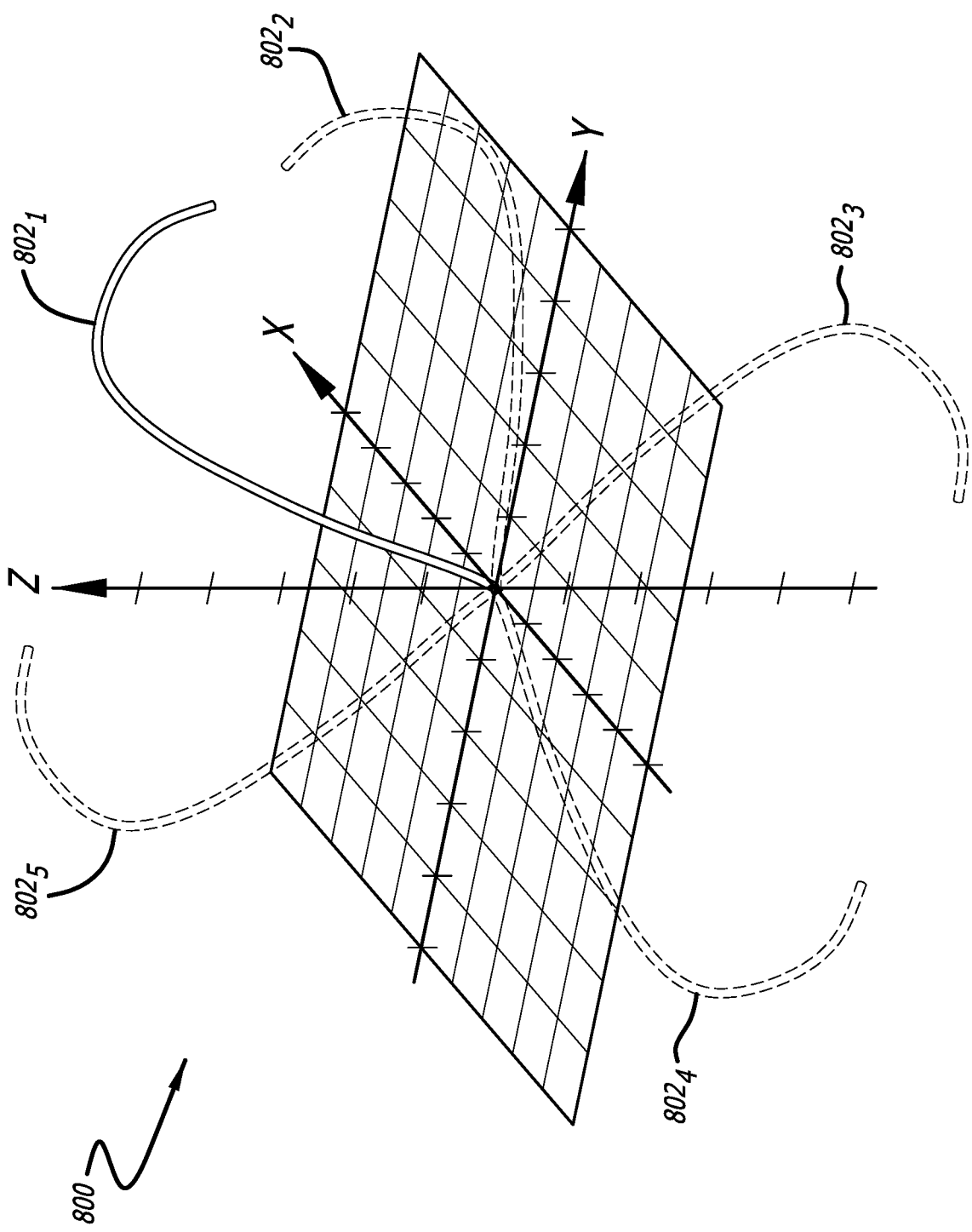
FIGS. 8A-8B are perspective illustrations of 3D catheter images within planes of 3D Cartesian coordinate systems in accordance with some embodiments in accordance with some embodiments.

Referring to FIG. 8A, a perspective illustration of 3D catheter images within a plane of a 3D Cartesian coordinate system is shown in accordance with some embodiments. Specifically, the plane 800 illustrates a Cartesian coordinate system for a three-dimensional space consisting of an ordered triplet of lines (axes) commonly referred to the x-axis, y-axis and z-axis, where a point within the plane 800 is represented by a numerical value along each axis as (x, y, z), often called "coordinates." The axes originate at a common point, which is often referred to as the "origin," having coordinates within the plane 800 of (0,0,0)

As seen in FIG. 8A, a plurality of 3D catheter images being 3D representations $802_1$-$802_i$ of the physical state of a stylet, i.e., the stylet 120, advancing through the vasculature of a patient's body. The 3D representations $802_1$-$802_i$ are computed from characteristics of reflected light signals by shape sensing logic as discussed above. However, what is notably missing from the computed characteristics of the reflected light signals 150 and the ensuing 3D representations $802_1$-$802_i$ is an indication of an orientation of the catheter relative to the patient's body.

Having knowledge of the orientation of the catheter relative to the patient's body is integral in generating and rendering a 2D display of the shape of the stylet (and/or catheter), as most, if not all, displays utilized in catheter tracking systems are 2D displays, e.g., such as the display 170. Thus, without an indication of the orientation of the catheter relative to the patient's body, a 2D display cannot be rendered that properly depicts the stylet on a display, e.g., the display 170, that is anatomically correct relative to the reference frame of the patient's body.

To further explain this problem, FIG. 8A illustrates the plurality of 3D representations $802_1$-$802_i$ of the physical state of a stylet advancing through the vasculature of a patient having various orientations within the plane 800. Each of the 3D representations $802_1$-$802_i$ may be in accordance with the characteristics of received reflected light signals, which merely indicate a shape such as a curve of the stylet without an indication as to a direction of the curve relative to a frame of reference. Thus, in order to generate and render a 2D display of the catheter relative to the reference frame of the patient's body, an orientation of the stylet must be determined in accordance with the reference frame of the patient's body.

Figure 8B:
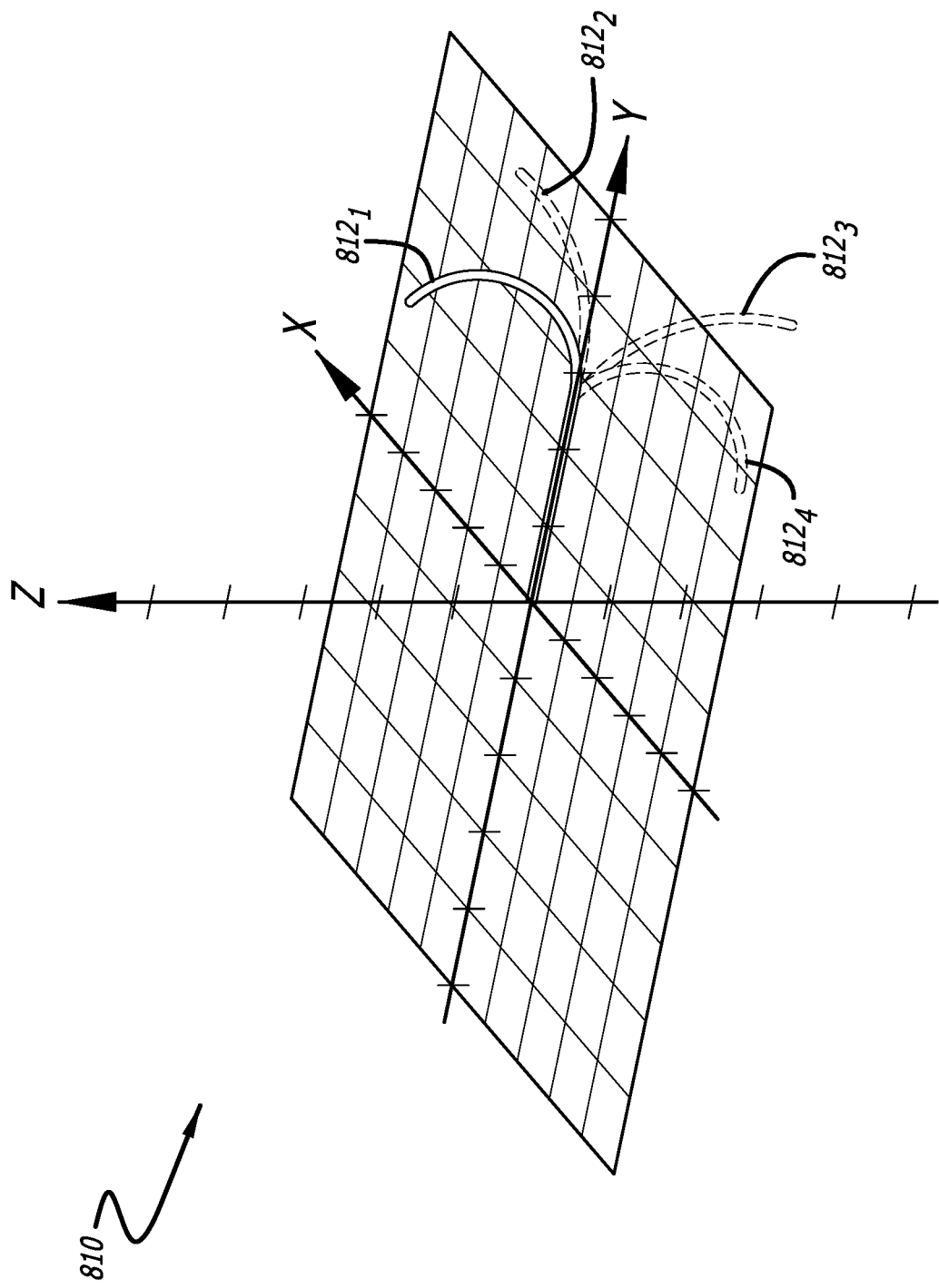

Referring to now FIG. 8B, a perspective illustration of 3D catheter images within the plane 810 of a 3D Cartesian coordinate system is shown in accordance with some embodiments. FIG. 8B illustrates a first step according to one embodiment of determining the orientation of the 3D representations $802_1$-$802_i$ of FIG. 8A. As discussed in further detail with respect to the embodiment of FIGS. 9A-9B, the percutaneous insertion site ("insertion site") of the stylet (and catheter, collectively referred to as the "stylet") may be known (e.g., on a patient's arm distal the elbow joint) and the initial direction that the stylet advances relative to the patient's body is known (e.g., toward the clavicle). As a result, a reference frame for the patient's body may be established by logic of the console in accordance with a coordinate system (such as an abstract x,y coordinate system) in relation to the patient. Therefore, the initial direction of the advancement of the stylet may be established as the positive direction along the y-axis with respect to the x,y coordinate system of the reference frame of the patient. As an illustrative example, FIG. 10 depicts of an exemplary embodiment of the medical instrument monitoring system illustrating an established reference frame 1020 of the patient, which is mirrored by an established reference frame 1022 of the display 170, with each frame of reference utilizing an x,y coordinate system.

Referring again to FIG. 8B, by constraining the initial direction of the advancement of the stylet to be in the positive direction along the y-axis, the reference frame establishment logic 196 may record and establish a correlation between initial reflected light received and the positive direction of the y-axis. Such a correlation may be stored by the reference frame establishment logic 196 and used to in defining the direction of the advancement of the stylet as discussed below. The term "initial reflected light" may refer to the portion of the received reflected light that corresponds to an indication that the stylet is traveling in a straight or substantially path. For example, with reference again to FIG. 10, the initial reflected light may correspond to the reflected light received while the stylet is advancing through segment 1002 of the patient 1000. Thus, a 2D depiction of the catheter advancing through the vasculature of the patient from the insertion site toward the patient's clavicle may be displayed on a 2D display based on the received reflected light and the constraint of the initial advancement of the stylet to be in the positive direction along the y-axis.

Continuing the example, as the stylet advances toward the clavicle, the stylet eventually begins to curve toward the patient's rib cage (i.e., toward the center of the patient's body). FIG. 8B illustrates the multiple scenarios that exist when the direction of the initial advancement of the stylet is known but the direction the stylet is curving is known. In other words, even though the direction of the initial advancement of the stylet is known, once the stylet begins to curve within the body, the received reflected light signals merely provide an indication of the angle of the curve, not direction of the curve relative to the reference frame of the patient.

Referring again to FIG. 10, the detection of the curve may occur as the stylet advances through the segment 1004. Referring now back to FIG. 8B, upon detection of the curvature of the stylet by the shape sensing logic 194, the frame reference establishment logic 196 establishes a correlation between the received reflected light and the positive direction along the x-axis. This is done based on knowledge that the stylet is constrained anatomically to curve toward the center of the patient's chest, which is in the positive direction along the x-axis in accordance with the established reference frame of the patient.

Thus, following detection of the curvature of the stylet, the frame reference establishment logic 196 establishes an orientation of the stylet, and thus, the catheter. By establishing a correlation between the initial reflected light and the positive direction along the y-axis and a correlation between reflected light corresponding to a curvature of the stylet, the frame reference establishment logic 196 can generate and render a 2D display illustrating a representation of the shape of the catheter during advancement through the vasculature of the patient having a proper anatomical orientation based on the reference frame of the patient's body. As the stylet continues its advancement, the shape sensing logic 194 in conjunction with the reference frame establishment logic 196 may generate a 2D display of the catheter by comparing the received reflected light with the orientation of the stylet defined by (i) the initial reflected light signals correlated with the positive direction along the y-axis of the reference frame of the patient, and (ii) the reflected light signals corresponding to the curve in the advancement correlated with the positive direction along the x-axis of the reference frame of the patient.

Figure 9A:
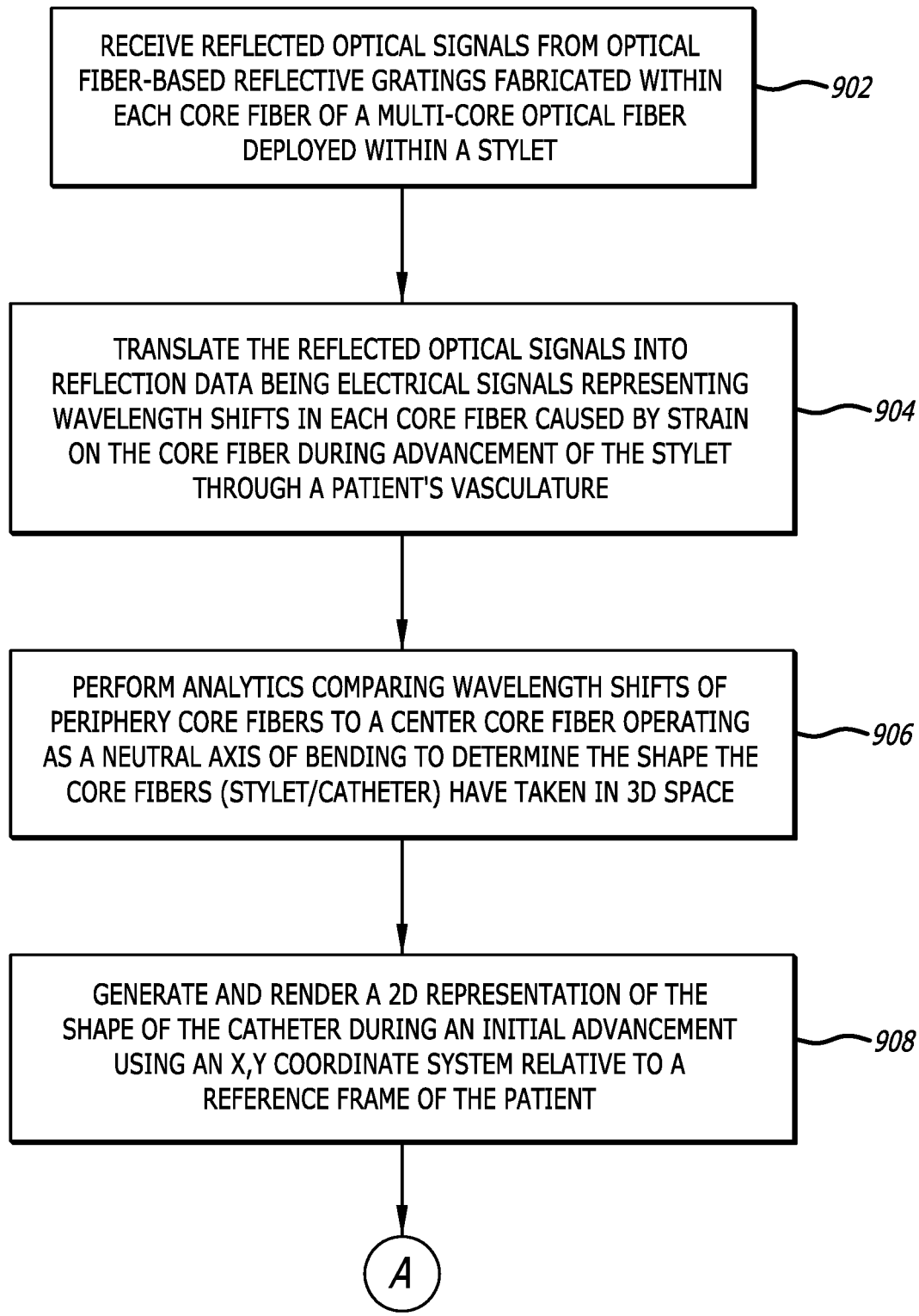
FIGS. 9A-9B illustrate a flowchart of a first embodiment of operations performed by logic of the medical instrument monitoring system of FIG. 1A in accordance with some embodiments.
Figure 9B:
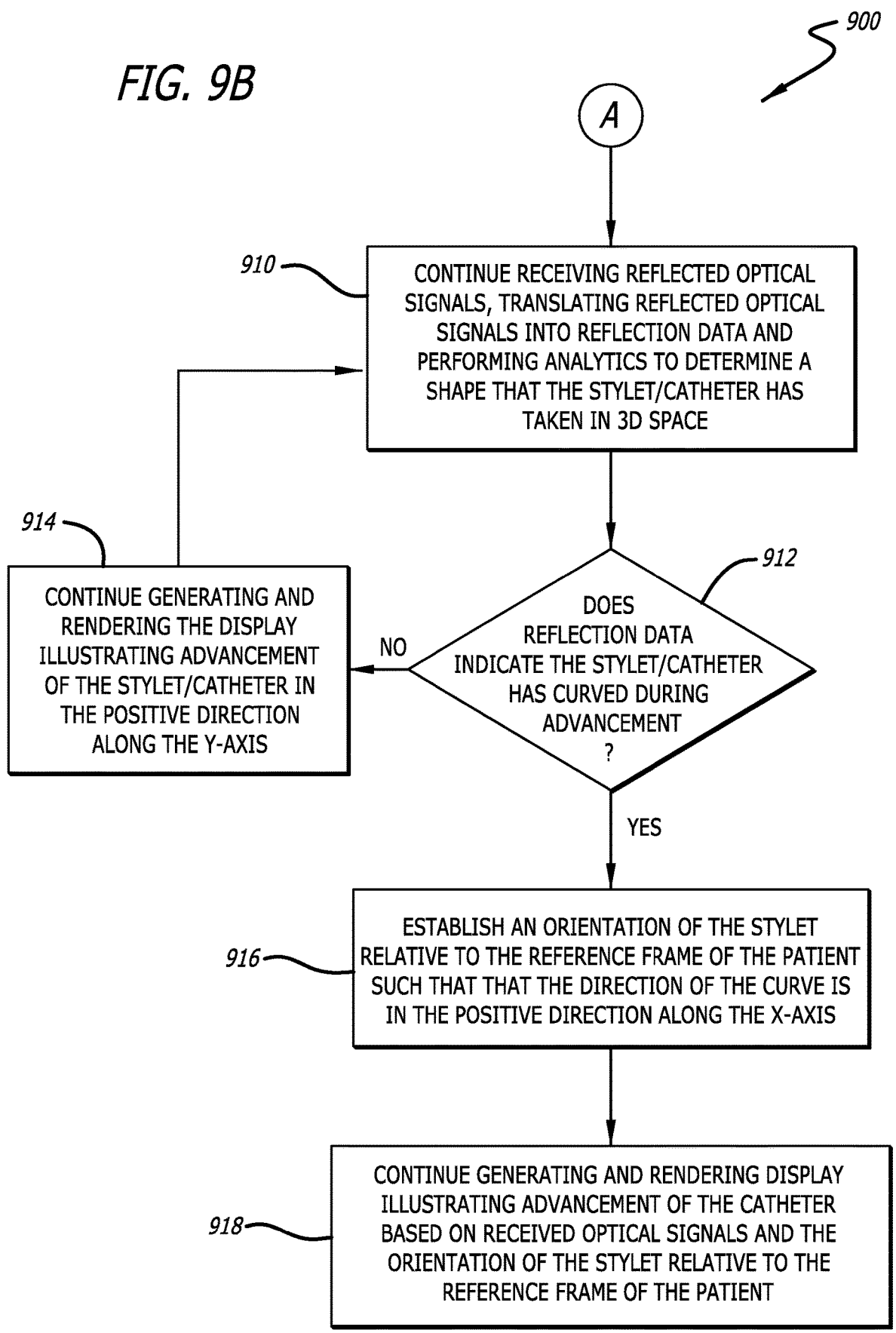
Figure 10:
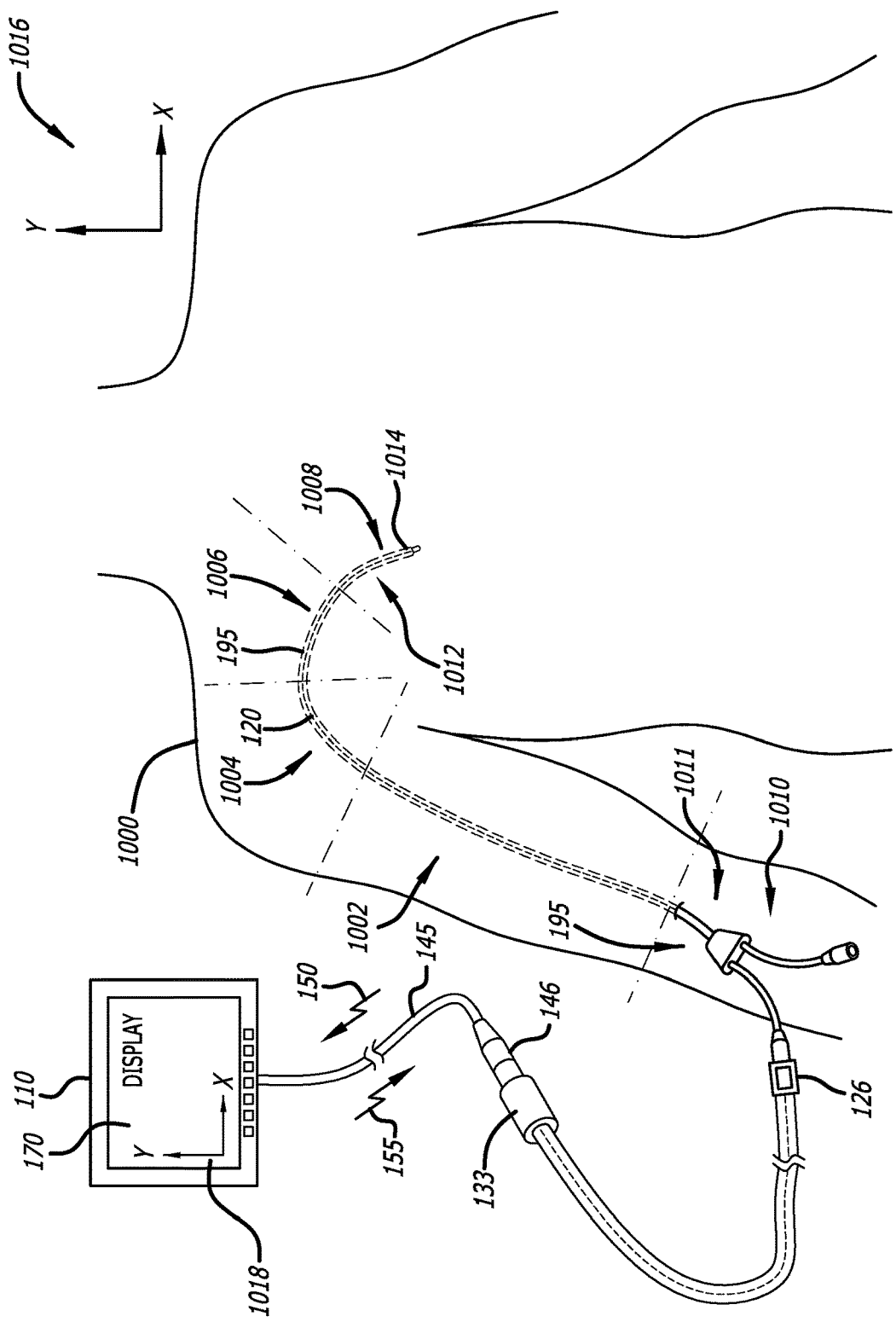
FIG. 10 is a second exemplary embodiment of the medical instrument monitoring system of FIG. 1A during operation and insertion of the catheter into a patient in accordance with some embodiments.

Referring now to FIGS. 9A-9B, a flowchart of a first embodiment of operations performed by logic of the medical instrument monitoring system of FIG. 1A is shown in accordance with some embodiments. Each block illustrated in FIGS. 9A-9B represents an operation performed in the method 900 of detecting an orientation of a catheter disposed within a patient's vasculature based on received reflect light signals. It is assumed that prior to the beginning of the method 900, a catheter having a stylet disposed therein has been inserted into the patient's vasculature at a known percutaneous insertion site (e.g., at a location on the patient's arm distal the elbow joint). Specifically, it is assumed that the stylet includes a multi-core optical fiber and is coupled to a console configured to provide broadband incident light to the stylet, such as the console 110 and the stylet 120 of FIG. 1A.

Thus, the method 900 begins when broadband incident light is received by and propagates along the multi-core optical fiber of the stylet. The broadband incident light is reflected by one or more gratings (sensors) of the multi-core optical fiber, such that the reflected light signals may include wavelength shifts that correlate with strain experienced by each sensor, as discussed above. The console receives the reflected optical signals (reflected light signals) from the gratings fabricated within each core fiber of the multi-core optical fiber deployed within the stylet (block 902).

The reflect light signals are then translated into reflection data being electrical signals representing wavelength shifts in each core fiber caused by strain on the core fiber during advancement of the stylet through the patient's vasculature (block 904). Analytics are then performed to compare the wavelength shifts of periphery core fibers to a center core fiber operating as a neutral axis of bending to determine the shape of core fibers (i.e., that which the stylet and the catheter) have taken in 3D space (block 906).

Following performance of analytics to determine a 3D shape of the catheter, a 2D display is generated and rendered to display a 2D representation of the shape of the catheter as the catheter advances through the patient's vasculature using an x,y coordinate system (block 908). The 2D display is rendered such that the initial advancement of the catheter is illustrated as being in the positive direction along the y-axis. As noted above, the x,y coordinate system of the display, such as the display 170 of FIG. 1A, corresponds to a reference frame that matches a reference frame of the patient's body. Thus, the 2D display of the catheter during its initial advancement matches the anatomical positioning of the catheter's initial advancement within the patient's body.

Referring now to FIG. 9B, reflected optical signals (light signals) continue to be received from the multi-core optical fiber providing a continued indication of the shape of the stylet, which corresponds to the advancement of the catheter within the patient's vasculature. Analytics are performed on the received reflected light signals in order to continue determining the shape that the stylet, and catheter, has taken in 3D shape in order to continue monitoring its advancement (block 910). As reflected light signals are continually received and the 3D shape of the catheter is determined during an initial advancement of the catheter, a determination is made as to whether the reflection data derived from the reflected light signals indicates that the stylet has curved during advancement (block 912). When a result of the determination is that the stylet has not curved (no at block 912), generation and display of the 2D display is continued in which the advancement of the catheter is illustrated in the positive direction along the y-axis of the reference frame of the display (e.g., the display 170) (block 914).

When a result of the determination is that the stylet has begun to curve (yes at block 912), an orientation of the stylet is established using the reference frame of the 2D display to match a reference frame of the patient's body (block 916). Specifically, the direction of the curve indicated by the reflected light signals is set to correlate with the positive direction along the x-axis of the 2D display. The orientation of the stylet with respect to the reference frame of the 2D display is established based on the direction of the initial advancement of the stylet being set to correlate with the positive direction along the y-axis and the direction of the curve being set to correlate with the positive direction along the x-axis. Thus, the logic of the console has established the orientation of the stylet (and catheter) such that display of the advancement of the catheter on the 2D display is illustrated in an anatomically proper manner with respect to the reference frame of the patient's body. The established orientation may be stored as the correlation of the reflected light signals (e.g., specific wavelength shifts) with a particular direction along a particular axis in the console, e.g., along with the reflect data 192 of FIGS. 1A-1B or, alternatively, in a separate datastore of console 110 not shown.

The 2D display is continually generated and rendered in order to illustrate advancement of the catheter based on received optical signals (light signals) utilizing the established orientation of the stylet (and catheter) with respect to the reference frame of the 2D display that matches that of the patient's body (block 918).

Referring to FIG. 10, a second exemplary embodiment of the medical instrument monitoring system of FIG. 1A during operation and insertion of a catheter including a stylet into a patient is shown in accordance with some embodiments. As noted above, FIG. 10 illustrates a series of theoretical segments of the stylet 120 (segments 1002, 1004, 1006, 1008), where each segment may indicate a transition from a first shape of the stylet 120 (and the catheter 195) to a second shape. As further illustrated, the catheter 195 generally includes a proximal portion 1011 that generally remains exterior to the patient 1000 and a distal portion 1012 that generally resides within the patient vasculature after placement is complete. The stylet 120 is employed to assist in the positioning of the distal tip 1014 of the catheter 195 in a desired position within the patient vasculature. In one embodiment, the desired position for the catheter distal tip 1014 is proximate the patient's heart, such as in the lower one-third ($\frac{1}{3}^{rd}$) portion of the Superior Vena Cava ("SVC") for this embodiment. Of course, the stylet 120 can be employed to place the catheter distal tip 1014 in other locations.

During advancement, the stylet 120 receives broadband light 155 from the console 110 via interconnect 145, which includes the connector 146 for coupling to the console connector 144 for the stylet assembly 118. The reflected light 150 from sensors (reflective gratings) within each core fiber of the multi-core optical fiber 137 are returned from the stylet 120 over the interconnect 145 for processing by the console 110. The physical state of the stylet 120 may be ascertained based on analytics of the wavelength shifts of the reflected light 150. For example, the strain caused through bending of the stylet 120, and hence angular modification of each core fiber, causes different degrees of deformation. The different degrees of deformation alters the shape of the sensors (reflective grating) positioned on the core fiber, which may cause variations (shifts) in the wavelength of the reflected light from the sensors positioned on each core fiber within the multi-core optical fiber 137, as shown in FIG. 2. From this wavelength shifting, the shape sensing analytic logic 194 within the console 110 may determine the physical state of the stylet 120 (e.g., shape, etc.), and as the catheter 195 mirrors the stylet 120, the physical state of the catheter 195 is also determined.

As discussed briefly above, FIG. 10 illustrates two references frames: a reference frame of the patient's body comprising the coordinate system 1016 relative to the patient's body; and a reference frame of the display 170 that mirrors the orientation of the reference frame of the patient's body and comprises the coordinate system 1018 relative to the boundaries of the display 170. Thus, referring to the embodiment of method 900 of FIGS. 9A-9B, the orientation of the reference frame of the patient's body (including the coordinate system 1016) is equivalent to the reference frame of the display 170 (including the coordinate system 1018). Thus, by determining an orientation of the stylet 120, and hence the catheter 195, the logic of the console 110 may generate a render a depiction of a 2D representation of the shape of the catheter 195 as it advances within the vasculature of the patient's body in an anatomically proper manner.

Figure 11B:
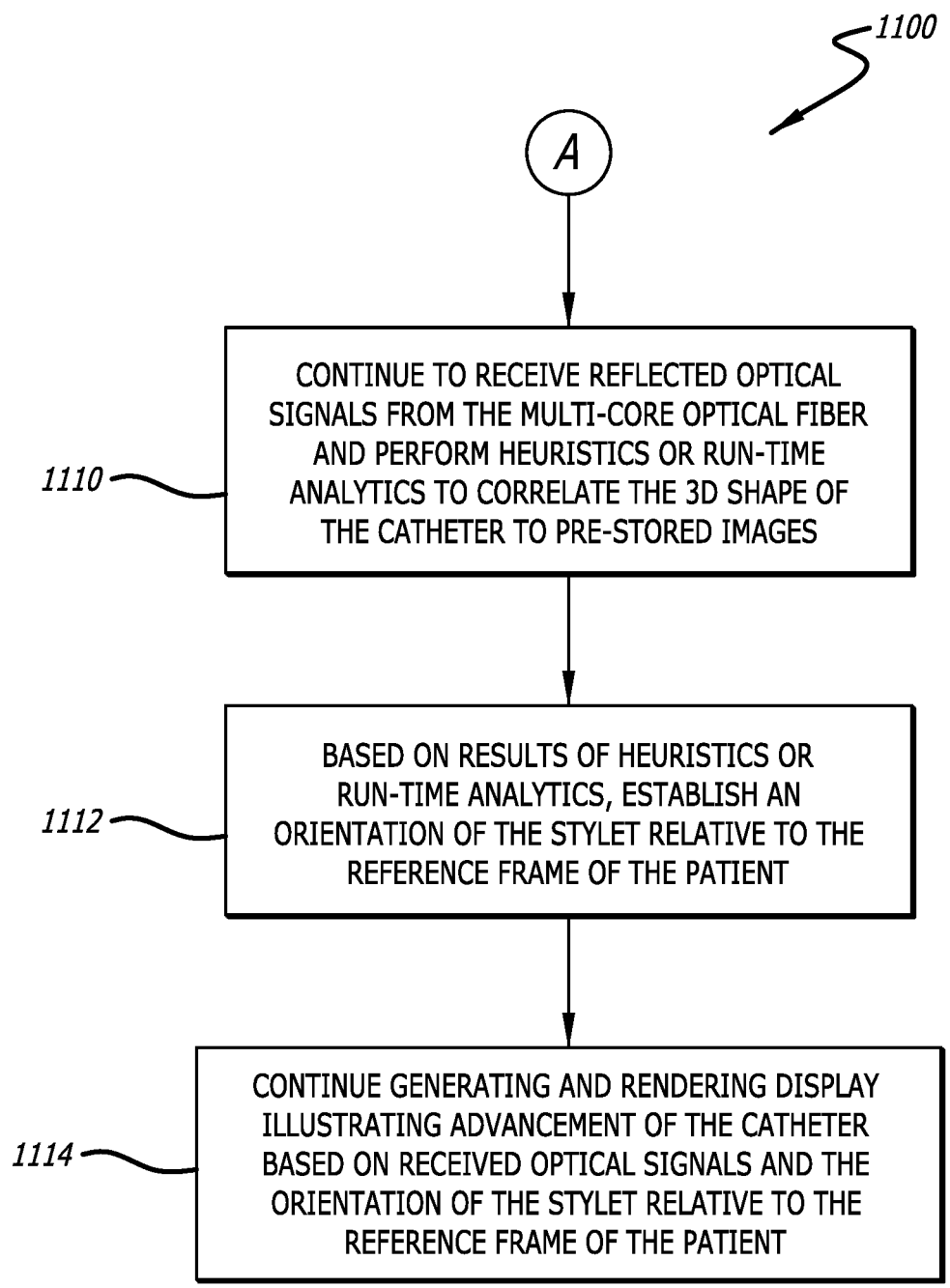

Referring to FIGS. 11A-11B, a flowchart of a second embodiment of operations performed by logic of the medical instrument monitoring system of FIG. 1A is shown in accordance with some embodiments. Each block illustrated in FIGS. 11A-11B represents an operation performed in the method 1100 of detecting an orientation of a catheter disposed within a patient's vasculature based on received reflect light signals. The assumptions discussed above with respect to the method 900 apply equally with respect to the method 1100.

Thus, the method 1100 begins when broadband incident light is received by and propagates along the multi-core optical fiber of the stylet. The broadband incident light is reflected by one or more gratings (sensors) of the multi-core optical fiber, such that the reflected light signals may include wavelength shifts that correlate with strain experienced by each sensor, as discussed above. The console receives the reflected optical signals (reflected light signals) from the gratings fabricated within each core fiber of the multi-core optical fiber deployed within the stylet (block 1102).

The reflect light signals are then translated into reflection data being electrical signals representing wavelength shifts in each core fiber caused by strain on the core fiber during advancement of the stylet through the patient's vasculature (block 1104). Analytics are then performed to compare the wavelength shifts of periphery core fibers to a center core fiber operating as a neutral axis of bending to determine the shape of core fibers (i.e., that which the stylet and the catheter) have taken in 3D space (block 1106).

Following performance of analytics to determine a 3D shape of the catheter, a 2D display is generated and rendered to display a 2D representation of the shape of the catheter as the catheter advances through the patient's vasculature using an x,y coordinate system relative to a reference frame of the patient as discussed above with respect to FIGS. 9A-9B (block 1108). The 2D display is rendered such that the direction of the initial advancement of the catheter is illustrated as being in the positive direction along the y-axis as discussed above with respect to FIGS. 9A-9B.

Referring now to FIG. 11B, reflected optical signals (light signals) continue to be received from the multi-core optical fiber providing a continued indication of the shape of the stylet, which corresponds to the advancement of the catheter within the patient's vasculature. Heuristics or run-time analytics are performed on the reflected light signals to correlate the 3D shape of the stylet to a plurality of pre-stored images (block 1110). In one such embodiment, a machine-learning model is provided with the current 3D shape of the stylet, which is processed to affect a correlation of the current 3D shape with pre-stored 3D images. The results of the processing of the machine-learning model indicate a correlation value between the current 3D shape and one or more of the pre-stored images, which each have a known orientation relative to the patient's body. Therefore, when a correlation value exceeds a threshold value, the current 3D shape is determined to have the known orientation of the corresponding pre-stored image. As would be understood by one of ordinary skill in the art, the machine-learning model would be pre-trained using the pre-stored images of 3D shapes of stylets/catheters each having a known orientation relative to the reference frame of the patient. Further, the machine-learning algorithm utilized may be any known machine-learning algorithm, especially, but not limited or restricted to supervised learning algorithms such as logistic regression and/or neural networks.

Thus, based on results of the heuristics or run-time analytics, an orientation of the stylet is established relative to the reference frame of the patient's body, which is mirrored by the reference frame of the 2D (block 1112). Thus, the console has established the orientation of the stylet (and catheter) such that display of the advancement of the catheter on the 2D display is illustrated in an anatomically proper manner with respect to the reference frame of the patient's body. The 2D display is continually generated and rendered in order to illustrate advancement of the catheter based on received optical signals (light signals) utilizing the established orientation of the stylet (and catheter) with respect to the reference frame of the 2D display that matches that of the patient's body (block 1114).

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical device system for placing a medical device into a body of a patient, the system comprising:
   the medical device comprising a multi-core optical fiber having a plurality of core fibers for experiencing different types of strain, each core fiber of the plurality of core fibers including a plurality of reflective gratings distributed along a longitudinal length of a corresponding core fiber and each reflective grating of the plurality of reflective gratings being configured to (i) reflect a light signal of a different spectral width based on received incident light, and (ii) change a characteristic of the light signal so reflected for use in determining a physical state of the multi-core optical fiber; and
   a console including one or more processors and a non-transitory computer-readable medium having stored thereon logic that, when executed by the one or more processors, causes operations including:
   providing a broadband incident light to the multi-core optical fiber,
   receiving reflected light signals of different spectral widths of the broadband incident light by each reflective grating of the plurality of reflective gratings, and
   processing the reflected light signals associated with the plurality of core fibers to determine (i) the physical state of the multi-core optical fiber relating to the medical device including the multi-core optical fiber, and (ii) an orientation of the multi-core optical fiber relative to a reference frame of the body, wherein processing the reflected light signals to determine the orientation of the multi-core optical fiber relative to the reference frame of the body includes:
   establishing the reference frame of the body utilizing a coordinate system;
   establishing an initial direction of advancement along a first axis of the coordinate system for the multi-core optical fiber based on the multi-core optical fiber entering the body at a known insertion site;
   correlating initial reflected light signals to the initial direction of advancement along the first axis of the coordinate system;
   detecting a curve in the advancement of the multi-core optical fiber based on processing of the reflected light signals; and
   correlating the reflected light signals corresponding to the curve in the advancement with a second direction of advancement along a second axis of the coordinate system, wherein the orientation is defined by (i) the initial reflected light signals correlated with the initial direction of advancement along the first axis of the coordinate system, and (ii) the reflected light signals corresponding to the curve in the advancement correlated with the second direction of advancement along the second axis of the coordinate system.

2. The system of claim 1, further comprising:
generating a display illustrating the physical state of the multi-core optical fiber based at least on the orientation determined during processing of the reflected light signals.

3. The system of claim 2, wherein the display is a two-dimensional representation of the physical state of the multi-core optical fiber in accordance with the orientation determined during processing of the reflected light signals.

4. The system of claim 1, wherein the physical state of the multi-core optical fiber relating to the medical device includes one or more of a length, a shape or a form as currently possessed by the multi-core optical fiber.

5. The system of claim 1, wherein the different types of strain include compression and tension.

6. The system of claim 1, wherein the medical device includes an elongated shape and is inserted into a vasculature of the body of the patient.

7. The system of claim 6, wherein the medical device is a stylet removably inserted into a lumen of a catheter assembly for placement of a distal tip of the catheter assembly in a superior vena cava of the vasculature.

8. The system of claim 1, wherein at least two core fibers of the plurality of core fibers experience the different types of strain in response to changes in the orientation of the multi-core optical fiber.

9. The system of claim 1, wherein each reflective grating of the plurality of reflective gratings alters its reflected light signal by applying a wavelength shift dependent on a type of strain of the different types of strain experienced by the multi-core optical fiber.

\* \* \* \* \*